US008703430B2

(12) United States Patent
Ogasawara et al.

(10) Patent No.: US 8,703,430 B2
(45) Date of Patent: *Apr. 22, 2014

(54) METHOD FOR MEASURING HUMAN MEGALIN

(75) Inventors: Shinya Ogasawara, Niigata (JP); Shuhei Miura, Niigata (JP); Akihiko Saito, Niigata (JP); Tetsuro Takeda, Niigata (JP)

(73) Assignees: Niigata University, Niigata (JP); Denka Seiken Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,984

(22) Filed: Apr. 26, 2011

(65) Prior Publication Data

US 2011/0195523 A1 Aug. 11, 2011

Related U.S. Application Data

(62) Division of application No. 12/293,992, filed as application No. PCT/JP2007/056660 on Mar. 28, 2007, now Pat. No. 7,955,809.

(30) Foreign Application Priority Data

Mar. 28, 2006 (JP) ................. 2006-089306

(51) Int. Cl.
*G01N 33/53* (2006.01)
(52) U.S. Cl.
USPC ............................................ 435/7.1; 435/7.2
(58) Field of Classification Search
None
See application file for complete search history.

(56) References Cited

U.S. PATENT DOCUMENTS

| 7,955,809 | B2 | 6/2011 | Ogasawara et al. |
| 2004/0204357 | A1 | 10/2004 | Brautigam et al. |
| 2004/0235161 | A1 | 11/2004 | Tabata et al. |
| 2007/0037232 | A1 | 2/2007 | Barasch et al. |
| 2009/0117594 | A1 | 5/2009 | Ogasawara et al. |
| 2010/0233738 | A1 | 9/2010 | Hara et al. |
| 2011/0195523 | A1 | 8/2011 | Ogasawara et al. |
| 2012/0219956 | A1 | 8/2012 | Devarajan et al. |

FOREIGN PATENT DOCUMENTS

| EP | 2 006 683 A1 | 12/2008 |
| EP | 2 426 495 A1 | 3/2012 |
| JP | 4-351962 | 12/1992 |
| JP | 8-105889 | 4/1996 |
| JP | 2005-528615 A | 9/2005 |
| JP | 2007-263750 A | 10/2007 |
| JP | 2007-536260 A | 12/2007 |
| JP | 2009-511913 A | 3/2009 |
| WO | WO 03/102493 A1 | 12/2003 |
| WO | WO-03/102593 A1 | 12/2003 |
| WO | WO-2005/107793 A2 | 11/2005 |
| WO | WO-2007/047458 A2 | 4/2007 |
| WO | WO-2009/041577 A1 | 4/2009 |

OTHER PUBLICATIONS

Norden et al. (J. Am. Soc. Nephrol. 2002 vol. 13, p. 125-133).*
Russian Office Action Application No. 2008142534/15 (055325) w/English translation.
http://www.abcam.com/index.html?t=115434&pt=1 downloaded Mar. 21, 2011.
Knox M.D. et al., HIV and community. Mental Healthcare. The Johns Hopkins University Press Ltd., London, 1998, p. 25.
http://www.biognosisltd.co.uk/Exocell/Urinary%20Assays.html downloaded Mar. 21, 2011.
Van Venrooij W.J. et al., Manual of Biological Markers of Disease, Kluwer Academic Publishers, the Netherlands, 1993, vol. 1, AMAN-C1.1/5.
Marion De Jong PhD et al., "Megalin is Essential for Renal Proximal Tubule Reabsorption of $^{111}$In-DTPA-Octreotide", The Journal of Nuclear Medicine, vol. 46, No. 10, Oct. 2005, pp. 1696-1700.
Supplementary European Search Report EP 07 74 0098 dated Aug. 24, 2009.
Arvi-Matti Kuusniemi et al., "Kidneys with heavy proteinuria show fibrosis, inflammation, and oxidative stress, but no tubular phenotypic change", Kidney International, vol. 68, (2005) pp. 121-132.
Anthony G. W. Norden et al., "Urinary Megalin Deficiency Implicates Abnormal Tubular Endocytic Function in Fanconi Syndrome", J. Am. Soc. Nephrol. 13: 125-133, 2002.
K. Kobayashi et al., "Conditions for Solubilization of Tamm-Horsfall Protein/Uromodulin in Human Urine and Establishment of a Sensitive and Accurate Enzyme-Linked Immunosorbent Assay (ELISA) Method", Archives of Biochemistry and Biophysics, vol. 388, No. 1, Apr. 1, 2001, pp. 113-120.
C.J. Ilsa Raats et al., "Reduction in Glomerular Heparan Sulfate Correlates with Complement Deposition and Albuminuria in Active Heymann Nephritis", J. Am. Soc. Nephrol. 10: 1689-1699, 1999.
Notice of Allowance U.S. Appl. No. 12/293,992 dated Feb. 8, 2011.
Final Office Action U.S. Appl. No. 12/293,992 dated Aug. 19, 2010.
Non-Final Office Action U.S. Appl. No. 12/293,992 dated Dec. 15, 2009.
Jordan (The Protein Protocol Handbook, second edition, edited by Walker, year 2000, p. 1083-1088).
Willnow et al. (PNAS 1996 vol. 93 p. 8460-8464).
Non-Final Office Action U.S. Appl. No. 12/293,992 dated Sep. 28, 2009.
EP Application No. 10769753.4, Search Report Dated Feb. 11, 2013.
Norden, A G W et al, "Urinary Megalin Deficiency Inplicates Abnormal Tubular Endocytic Function in Fanconi Syndrome", Journal of the American Society of Nephrology, Williams and Wilkins, Baltimore, MD, US, vol. 13, Jan. 1, 2002, p. 125-133.

(Continued)

*Primary Examiner* — Jacob Cheu
(74) *Attorney, Agent, or Firm* — Foley & Lardner LLP

(57) ABSTRACT

This invention provides a method for measuring human megalin that can be performed in a simpler manner within a shorter period of time than is possible with conventional techniques, and that can also quantify human megalin. This invention also provides a method that enables diagnosis of functional diseases, which are specific to cells, tissues, or organs, in a site-directed manner at an early stage. Measurement of human megalin enables detection of a disease in an organ in which megalin expression is observed.

4 Claims, 4 Drawing Sheets

(56) References Cited

OTHER PUBLICATIONS

Ogasawara, Shinya et al., "Significance of Urinary Full-Legnth and Ectodomain Forms of Megalin in Patients With Type 2 Diabetes.", Diabetes Care May 2012 LNKD-Pubmed: 22410816, vol. 35, No. 5, May 2012, p. 1112-1118.
Thrailkill, K.M. et al., "Microalbuminuria in Type 1 Diabetes is Associated With Enhanced Excretion of the Endocytic Multiligand Receptors Megalin and Cubilin", Diabetes Care, Vol. 32, No. 7, Apr. 14, 2009, p. 1266-1268.
Wilmer, Martijn et al., "Urinary Protein Excretion Pattern and Renal Expression of Megalin and Cubilin in Nephropathic Cystinosis.", American Journal of Kidney Diseases, vol. 51, Jan. 1, 2008, p. 893-903.
EP Application No. 10769741.9, Search Report Dated Jan. 9, 2013.
Zheng et al., "Megalin (gp330): a putative endocytic receptor for thyroglobulin (Tg)," *Endocrinology*;, vol. 139, No. 3, pp. 1462-1465 (1998).
Gburek et al., "Renal uptake of myoglobin is mediated by the endocytic receptors megalin and cubilin", Am J Physiol Renal Physiol 285: F451-F458, 2003.
International Search Report in PCT/JP2007/056660 dated May 15, 2007.
International Search Report PCT/JP2010/057465 dated Aug. 3, 2010.
International Search Report PCT/JP2010/057490 dated Jun. 8, 2010.
Office Action in U.S. Appl. No. 13/266,397 dated Jan. 22, 2013.
Saito et al., "Megalin, a Multiligand Endocytotic Receptor: The Role in the Development of Diabetic Nephropathy, Metabolic Syndrome—related Nephropathy and Uremia", Niigata Medical Journal, 119(1), Jan. 10, 2005, pp. 1-5.
Yamazaki et al., "All Four Putative Ligand-Binding Domains in Megalin Contain Pathogenic Epitopes Capable of Inducing Passive Heymann Nephritis", J. Am. Soc. Nephrol., 1998, vol. 9, 1638-1644.
De Jong et al., "Megalin is Essential for Renal Proximal Tubule Reabsorption of 111In-DTPA-Octreotide," The Journal of Nuclear Medicine, vol. 46, No. 10, pp. 1696-1700 (2005).
Zheng et al., "Megalin (gp330): a putative endocytic receptor for thyroglobulin (Tg)," *Endocrinology*, vol. 193, No. 2, pp. 1462-1465 (1998).
Examination Report issued in related Indian Patent Application No. 5815/CHENP/2008 dated Jun. 25, 2013.
Notice of Allowance issued in related U.S. Appl. No. 13/266,411, dated Oct. 16, 2013.
Notice of Allowance issued in related U.S. Appl. No. 13/266,397, dated Sep. 20, 2013.
Office Action in JP Appln. No. 2009-108498 dated Jul. 30, 2013.
Office Action in JP Appln No. 2009-108498 dated Jul. 30, 2013.

\* cited by examiner

SEQUENCE LISTING

<160> NUMBER OF SEQ ID NOS: 2

<210> SEQ ID NO 1
<211> LENGTH: 13968
<212> TYPE: DNA
<213> ORGANISM: Homo sapiens

<400> SEQUENCE: 1

| | | | | | | |
|---|---|---|---|---|---|---|
| atggatcgcg | ggccggcagc | agtggcgtgc | acgctgctcc | tggctctcgt | cgcctgccta | 60 |
| gcgccggcca | gtggccaaga | atgtgacagt | gcgcattttc | gctgtggaag | tgggcattgc | 120 |
| atccctgcag | actggaggtg | tgatgggacc | aaagactgtt | cagatgacgc | ggatgaaatt | 180 |
| ggctgcgctg | ttgtgacctg | ccagcagggc | tatttcaagt | gccagagtga | gggacaatgc | 240 |
| atccccagct | cctgggtgtg | tgaccaagat | caagactgtg | atgatggctc | agatgaacgt | 300 |
| caagattgct | cacaaagtac | atgctcaagt | catcagataa | catgctccaa | tggtcagtgt | 360 |
| atcccaagtg | aatacaggtg | cgaccacgtc | agagactgcc | ccgatggagc | tgatgagaat | 420 |
| gactgccagt | acccaacatg | tgagcagctt | acttgtgaca | atgggggcctg | ctataacacc | 480 |
| agtcagaagt | gtgattggaa | agttgattgc | agggactcct | cagatgaaat | caactgcact | 540 |
| gagatatgct | tgcacaatga | gttttcatgt | ggcaatggag | agtgtatccc | tcgtgcttat | 600 |
| gtctgtgacc | atgacaatga | ttgccaagac | ggcagtgatg | aacatgcttg | caactatccg | 660 |
| acctgcggtg | gttaccagtt | cacttgcccc | agtggccgat | gcatttatca | aaactggtt | 720 |
| tgtgatggag | aagatgactg | taaagataat | ggagatgaag | atggatgtga | aagcggtcct | 780 |
| catgatgttc | ataaatgttc | cccaagagaa | tggtcttgcc | cagagtcggg | acgatgcatc | 840 |
| tccatttata | agtttgtga | tgggatttta | gattgcccag | aagagaaga | tgaaaacaac | 900 |
| actagtaccg | aaaatactg | tagtatgact | ctgtgctctg | ccttgaactg | ccagtaccag | 960 |
| tgccatgaga | cgccgtatgg | aggagcgtgt | ttttgtcccc | caggttatat | catcaaccac | 1020 |
| aatgacagcc | gtacctgtgt | tgagtttgat | gattgccaga | tatggggaat | ttgtgaccag | 1080 |
| aagtgtgaaa | gccgacctgg | ccgtcacctg | tgccactgtg | aagaagggta | tatcttggag | 1140 |
| cgtggacagt | attgcaaagc | taatgattcc | tttgcgagg | cctccattat | cttctccaat | 1200 |
| ggtcgggatt | tgttaattgg | tgatattcat | ggaaggagct | tccggatcct | agtggagtct | 1260 |
| cagaatcgtg | gagtggccgt | gggtgtggct | ttccactatc | acctgcaaag | agttttttgg | 1320 |
| acagacaccg | tgcaaaataa | ggtttttca | gttgacatta | atggtttaaa | tatccaagag | 1380 |
| gttctcaatg | tttctgttga | aaccccagag | aacctggctg | tggactgggt | taataataaa | 1440 |
| atctatctag | tggaaaccaa | ggtcaaccgc | atagatatgg | taaatttgga | tggaagctat | 1500 |
| cgggttaccc | ttataactga | aaacttgggg | catcctagag | gaattgccgt | ggacccaact | 1560 |
| gttggttatt | tattttctc | agattgggag | agccttctg | gggaacctaa | gctggaaagg | 1620 |
| gcattcatgg | atggcagcaa | ccgtaaagac | ttggtgaaaa | caaagctggg | atggcctgct | 1680 |
| ggggtaactc | tggatatgat | atcgaagcgt | gtttactggg | ttgactctcg | gtttgattac | 1740 |
| attgaaactg | taacttatga | tggaattcaa | aggaagactg | tagttcatgg | aggctccctc | 1800 |
| attcctcatc | cctttggagt | aagcttattt | gaaggtcagg | tgttctttac | agattggaca | 1860 |
| aagatggccg | tgctgaaggc | aaacaagttc | acagagacca | acccacaagt | gtactaccag | 1920 |
| gcttccctga | ggcccatgg | agtgactgtt | taccattccc | tcagacagcc | ctatgctacc | 1980 |
| aatccgtgta | aagataacaa | tgggggctgt | gagcaggtct | gtgttctcag | ccacagaaca | 2040 |

```
gataatgatg gtttgggttt ccgttgcaag tgcacattcg gcttccaact ggatacagat    2100
gagcgccact gcattgctgt tcagaatttc ctcattttt catcccaagt tgctattcgt    2160
gggatcccgt tcaccttgtc tacccaggaa gatgtcatgg ttccagtttc ggggaatcct    2220
tctttctttg tcgggattga ttttgacgcc caggacagca ctatctttt ttcagatatg    2280 tcaaaacaca tgattttaa gcaaaagatt gatggcacag gaagagaaat tctcgcagct    2340
aacagggtgg aaaatgttga aagtttggct tttgattgga tttcaaagaa tctctattgg    2400
acagactctc attacaagag tatcagtgtc atgaggctag ctgataaaac gagacgcaca    2460
gtagttcagt atttaaataa cccacggtcg gtggtagttc atcctttgc cgggtatcta    2520 ttcttcactg attggttccg tcctgctaaa attatgagag catggagtga cggatctcac    2580
ctcttgcctg taataaacac tactcttgga tgcccaatg gcttggccat cgattgggct    2640
gcttcacgat tgtactgggt agatgcctat tttgataaaa ttgagcacag caccttgat    2700 ggtttagaca gaagaagact gggccatata gagcagatga cacatccgtt tggacttgcc    2760
atctttggag agcatttatt ttactgac tggagactgg gtgccattat tcgagtcagg    2820
aaagcagatg tggagaaat gacagttatc cgaagtggca ttgcttacat actgcatttg    2880
aaatcgtatg atgtcaacat ccagactggt tctaacgcct gtaatcaacc cacgcatcct    2940
aacggtgact gcagccactt ctgcttcccg gtgccaaatt tccagcgagt gtgtgggtgc    3000
ccttatggaa tgaggctggc ttccaatcac ttgacatgcg aggggaccc aaccaatgaa    3060 ccacccacgg agcagtgtgg cttattttcc ttccctgta aaaatggcag atgtgtgccc    3120
aattactatc tctgtgatgg agtcgatgat tgtcatgata acagtgatga gcaactatgt    3180
ggcacactta ataatacctg ttcatcttcg gcgttcacct gtggccatgg ggagtgcatt    3240
cctgcacact ggcgctgtga caaacgcaac gactgtgtgg atggcagtga tgagcacaac    3300
tgccccaccc acgcacctgc ttcctgcctt gacacccaat acacctgtga taatcaccag    3360
tgtatctcaa agaactgggt ctgtgacaca gacaatgatt gtggggatgg atctgatgaa    3420
aagaactgca attcgacaga gacatgccaa cctagtcagt ttaattgccc caatcatcga    3480
tgtattgacc tatcgtttgt ctgtgatggt gacaaggatt gtgttgatgg atctgatgag    3540
gttggttgtg tattaaactg tactgcttct caattcaagt gtgccagtgg ggataaatgt    3600
attggcgtca caaatcgttg tgatggtgtt tttgattgca gtgacaactc ggatgaagcg    3660
ggctgtccaa ccaggcctcc tggtatgtgc cactcagatg aatttcagtg ccaagaagat    3720
ggtatctgca teccgaactt ctgggaatgt gatgggcatc cagactgcct ctatggatct    3780
gatgagcaca tgcctgtgt ccccaagact tgccccttcat catatttcca ctgtgacaac    3840
ggaaactgca tccacagggc atggctctgt gatcgggaca atgactgcgg ggatatgagt    3900
gatgagaagg actgccctac tcagcccttt cgctgtccta gttggcaatg gcagtgtctt    3960
ggccataaca tctgtgtgaa tctgagtgta gtgtgtgatg gcatctttga ctgccccaat    4020
gggacagatg agtccccact ttgcaatggg aacagctgct cagatttcaa tggtggttgt    4080
actcacgagt gtgttcaaga gcccctttggg gctaaatgcc tatgtccatt gggattctta    4140
cttgccaatg attctaagac ctgtgaagac atagatgaat gtgatattct aggctcttgt    4200
agccagcact gttacaatat gagaggttct ttccggtgct cgtgtgatac aggctacatg    4260
ttagaaagtg atgggaggac ttgcaaagtt acagcatctg agagtctgct gttacttgtg    4320
gcaagtcaga acaaaattat tgccgacagt gtcacctccc aggtccacaa tatctattca    4380
ttggtcgaga atggttctta cattgtagct gttgattttg attcaattag tggtcgtatc    4440
```

```
ttttggtctg atgcaactca gggtaaaacc tggagtgcgt ttcaaaatgg aacggacaga    4500
agagtggtat ttgacagtag catcatcttg actgaaacta ttgcaataga ttgggtaggt    4560
cgtaatcttt actggacaga ctatgctctg gaaacaattg aagtctccaa aattgatggg    4620
agccacagga ctgtgctgat tagtaaaaac ctaacaaatc caagaggact agcattagat    4680
cccagaatga atgagcatct actgttctgg tctgactggg gccaccaccc tcgcatcgag    4740
cgagccagca tggacggcag catgcgcact gtcattgtcc aggacaagat cttctggccc    4800
tgcggcttaa ctattgacta ccccaacaga ctgctctact tcatggactc ctatcttgat    4860
tacatggact tttgcgatta taatggacac catcggagac aggtgatagc cagtgatttg    4920
attatacggc acccctatgc cctaactctc tttgaagact ctgtgtactg gactgaccgt    4980
gctactcgtc gggttatgcg agccaacaag tggcatggag ggaaccagtc agttgtaatg    5040
tataatattc aatggcccct tgggattgtt gcggttcatc cttcgaaaca accaaattcc    5100
gtgaatccat gtgccttttc ccgctgcagc catctctgcc tgctttcctc acaggggcct    5160
cattttact cctgtgtttg tccttcagga tggagtctgt ctcctgatct cctgaattgc    5220
ttgagagatg atcaaccttt cttaataact gtaaggcaac atataatttt tggaatctcc    5280
cttaatcctg aggtgaagag caatgatgct atggtcccca tagcagggat acagaatggt    5340
ttagatgttg aatttgatga tgctgagcaa tacatctatt gggttgaaaa tccaggtgaa    5400
attcacagag tgaagacaga tggcaccaac aggacagtat ttgcttctat atctatggtg    5460
gggccttcta tgaacctggc cttagattgg atttcaagaa acctttattc taccaatcct    5520
agaactcagt caatcgaggt tttgacactc cacggagata tcagatacag aaaaacattg    5580
attgccaatg atgggacagc tcttggagtt ggctttccaa ttggcataac tgttgatcct    5640
gctcgtggga agctgtactg gtcagaccaa ggaactgaca gtggggttcc tgccaagatc    5700
gccagtgcta acatggatgg cacatctgtg aaaactctct ttactgggaa cctcgaacac    5760
ctggagtgtg tcactcttga catcgaagag cagaaactct actgggcagt cactggaaga    5820
ggagtgattg aaagaggaaa cgtggatgga acagatcgga tgatcctggt acaccagctt    5880
tcccacccct ggggaattgc agtccatgat tctttccttt attatactga tgaacagtat    5940
gaggtcattg aaagagttga taaggccact ggggccaaca aaatagtctt gagagataat    6000
gttccaaatc tgagggggtct tcaagtttat cacagacgca atgccgccga atcctcaaat    6060
```
```
ggctgtagca acaacatgaa tgcctgtcag cagatttgcc tgcctgtacc aggaggattg    6120
ttttcctgcg cctgtgccac tggatttaaa ctcaatcctg ataatcggtc ctgctctcca    6180
tataactctt tcattgttgt ttcaatgctg tctgcaatca gaggctttag cttggaattg    6240
tcagatcatt cagaaaccat ggtgccggtg gcaggccaag acgaaacgc actgcatgtg    6300
gatgtggatg tgtcctctgg ctttatttat tggtgtgatt ttagcagctc agtggcatct    6360
gataatgcga tccgtagaat taaaccagat ggatcttctc tgatgaacat tgtgacacat    6420
ggaataggag aaaatggagt ccggggtatt gcagtggatt gggtagcagg aaatctttat    6480
ttcaccaatg cctttgtttc tgaaacactg atagaagttc tgcggatcaa tactacttac    6540
cgccgtgttc ttcttaaagt cacagtggac atgcctaggc atattgttgt agatcccaag    6600
aacagatacc tcttctgggc tgactatggg cagagaccaa agattgagcg ttcttttcctt    6660
gactgtacca atcgaacagt gcttgtgtca gagggcattg tcacaccacg gggcttggca    6720
gtggaccgaa gtgatggcta cgtttattgg gttgatgatt ctttagatat aaattgcaagg    6780
attcgtatca atggagagaa ctctgaagtg attcgttatg gcagtcgtta cccaactcct    6840
```

```
tatggcatca ctgttttga aaattctatc atatgggtag ataggaattt gaaaaagatc    6900
ttccaagcca gcaaggaacc agagaacaca gagccaccca cagtgataag agacaatatc    6960
aactggctaa gagatgtgac catctttgac aagcaagtcc agccccggtc accagcagag    7020
gtcaacaaca acccttgctt ggaaaacaat ggtgggtgct ctcatctctg ctttgctctg    7080
cctggattgc acaccccaaa atgtgactgt gcctttggga ccctgcaaag tgatggcaag    7140
aattgtgcca tttcaacaga aaatttcctc atctttgcct tgtctaattc cttgagaagc    7200
ttacacttgg accctgaaaa ccatagccca ccttccaaa caataaatgt ggaaagaact    7260
gtcatgtctc tagactatga cagtgtaagt gatagaatct acttcacaca aaatttagcc    7320
tctggagttg gacagatttc ctatgccacc ctgtcttcag ggatccatac tccaactgtc    7380
attgcttcag gtatagggac tgctgatggc attgccttg actggattac tagaagaatt    7440
tattacagtg actacctcaa ccagatgatt aattccatgg ctgaagatgg gtctaaccgc    7500
actgtgatag cccgcgttcc aaaaccaaga gcaattgtgt tagatccctg ccaagggtac    7560
ctgtactggg ctgactggga tacacatgcc aaaatcgaga gagccacatt gggaggaaac    7620
ttccgggtac ccattgtgaa cagcagtctg gtcatgccca gtgggctgac tctggactat    7680
gaagaggacc ttctctactg ggtggatgct agtctgcaga ggattgaacg cagcactctg    7740
acgggcgtgg atcgtgaagt cattgtcaat gcagccgttc atgcttttgg cttgactctc    7800
tatgccagt atatttactg gactgacttg tacacacaaa gaatttaccg agctaacaaa    7860
tatgacgggt caggtcagat tgcaatgacc acaaatttgc tctcccagcc caggggaatc    7920
aacactgttg tgaagaacca gaaacaacag tgtaacaatc cttgtgaaca gtttaatggg    7980
ggctgcagcc atatctgtgc accaggtcca aatggtgccg agtgccagtg tccacatgag    8040
ggcaactggt atttggccaa caacaggaag cactgcattg tggacaatgg tgaacgatgt    8100
ggtgcatctt ccttcacctg ctccaatggg cgctgcatct cggaagagtg gaagtgtgat    8160
aatgacaacg actgtgggga tggcagtgat gagatggaaa gtgtctgtgc acttcacacc    8220
tgctcaccga cagccttcac ctgtgccaat gggcgatgtg tccaatactc ttaccgctgt    8280
gattactaca atgactgtgg tgatggcagt gatgaggcag ggtgcctgtt cagggactgc    8340
aatgccacca cggagtttat gtgcaataac agaaggtgca tacctcgtga gtttatctgc    8400
aatggtgtag acaactgcca tgataataac acttcagatg agaaaaattg ccctgatcgc    8460
acttgccagt ctggatacac aaaatgtcat aattcaaata tttgtattcc tcgcgtttat    8520
ttgtgtgacg gagacaatga ctgtggagat aacagtgatg aaaaccctac ttattgcacc    8580
actcacacat gcagcagcag tgagttccaa tgcgcatctg ggcgctgtat tcctcaacat    8640
tggtattgtg atcaagaaac agattgtttt gatgcctctg atgaacctgc tcttgtggt    8700
cactctgagc gaacatgcct agctgatgag ttcaagtgtg atggtgggag gtgcatccca    8760
agcgaatgga tctgtgacgg tgataatgac tgtgggata tgagtgacga ggataaaagg    8820
caccagtgtc agaatcaaaa ctgctcggat tccgagtttc tctgtgtaaa tgacagacct    8880
ccggacagga ggtgcattcc ccagtcttgg gtctgtgatg gcgatgtgga ttgtactgac    8940
ggctacgatg agaatcagaa ttgcaccagg agaacttgct ctgaaaatga attcacctgt    9000
ggttacggac tgtgtatccc aaagatattc aggtgtgacc ggcacaatga ctgtggtgac    9060
tatagcgacg agagggctg cttataccag acttgccaac agaatcagtt tacctgtcag    9120
aacgggcgct gcattagtaa aaccttcgtc tgtgatgagg ataatgactg tggagacgga    9180
tctgatgagc tgatgcacct gtgccacacc ccagaaccca cgtgtccacc tcacgagttc    9240
```

```
aagtgtgaca atgggcgctg catcgagatg atgaaactct gcaaccacct agatgactgt   9300
ttggacaaca gcgatgagaa aggctgtggc attaatgaat gccatgaccc ttcaatcagt   9360
ggctgcgatc acaactgcac agacaccttta accagtttct attgttcctg tcgtcctggt   9420
tacaagctca tgtctgacaa gcggacttgt gttgatattg atgaatgcac agagatgcct   9480
tttgtctgta gccagaagtg tgagaatgta ataggctcct acatctgtaa gtgtgcccca   9540
ggctacctcc gagaaccaga tggaaagacc tgccggcaaa acagtaacat cgaaccctat   9600
ctcattttta gcaaccgtta ctatttgaga aatttaacta tagatggcta ttttttactcc   9660 ctcatcttgg aaggactgga caatgttgtg gcattagatt ttgaccgagt agagaagaga   9720
ttgtattgga ttgatacaca gaggcaagtc attgagagaa tgtttctgaa taagacaaac   9780
aaggagacaa tcataaacca cagactacca gctgcagaaa gtctggctgt agactgggtt   9840
tccagaaagc tctactggtt ggatgcccgc ctggatggcc tctttgtctc tgacctcaat   9900
ggtggacacc gccgcatgct ggcccagcac tgtgtggatg ccaacaacac cttctgcttt   9960
gataatccca gaggacttgc ccttcacccct caatatgggt acctctactg ggcagactgg  10020
ggtcaccgcg catacattgg gagagtaggc atggatggaa ccaacaagtc tgtgataatc  10080
tccaccaagt tagagtggcc taatggcatc accattgatt acaccaatga tctactctac  10140
tgggcagatg cccacctggg ttacatagag tactctgatt tggagggcca ccatcgacac  10200
acggtgtatg atggggcact gcctcacccct ttcgctatta ccattttttga agacactatt  10260 tattggacag attggaatac aaggacagtg gaaaagggaa acaaatatga tggatcaaat  10320
agacagacac tggtgaacac aacacacaga ccatttgaca tccatgtgta ccatccatat  10380
aggcagccca ttgtgagcaa tccctgtggt accaacaatg gtggctgttc tcatctctgc  10440
ctcatcaagc caggaggaaa agggttcact tgcgagtgtc cagatgactt ccgcacccct  10500
caactgagtg gcagcaccta ctgcatgccc atgtgctcca gcacccagtt cctgtgcgct  10560
aacaatgaaa agtgcattcc tatctggtgg aaatgtgatg acagaaaga ctgctcagat  10620 ggctctgatg aactggccct ttgccccgcag cgcttctgcc gactgggaca gttccagtgc  10680
agtgacggca actgcaccag cccgcagact ttatgcaatg ctcaccaaaa ttgccctgat  10740
gggtctgatg aagaccgtct tcttttgtgag aatcaccact gtgactccaa tgaatggcag  10800
tgcgccaaca aacgttgcat cccagaatcc tggcagtgtg acacatttaa cgactgtgag  10860
gataactcag atgaagacag ttcccactgt gccagcagga cctgccggcc gggccagttt  10920
cggtgtgcta atggccgctg catcccgcag gcctggaagt gtgatgtgga taatgattgt  10980
ggagaccact cggatgagcc cattgaagaa tgcatgagct ctgcccatct ctgtgacaac  11040
ttcacagaat tcagctgcaa aacaaattac cgctgcatcc caagtgggc cgtgtgcaat  11100 ggtgtagatg actgcaggga caacagtgat gagcaaggct gtgaggagag gacatgccat  11160
cctgtggggg atttccgctg taaaaatcac cactgcatcc ctcttcgttg gcagtgtgat  11220
gggcaaaatg actgtggaga taactcagat gaggaaaact gtgctccccg ggagtgcaca  11280
gagagcgagt tcgatgtgt caatcagcag tgcattccct cgcgatggat ctgtgaccat  11340
tacaacgact gtgggacaa ctcagatgaa cgggactgtg agatgaggac ctgccatcct  11400
gaatattttc agtgtacaag tggacattgt gtacacagtg aactgaaatg cgatggatcc  11460
gctgactgtt tggatgcgtc tgatgaagct gattgtccca cacgctttcc tgatggtgca  11520
tactgccagg ctactatgtt cgaatgcaaa aaccatgttt gtatcccgcc atattggaaa  11580
tgtgatggcg atgatgactg tggcgatggt tcagatgaag aacttcacct gtgcttggat  11640
```

```
gttccctgta attcaccaaa ccgtttccgg tgtgacaaca atcgctgcat ttatagtcat    11700
gaggtgtgca atggtgtgga tgactgtgga gatggaactg atgagacaga ggagcactgt    11760
agaaaaccga cccctaaacc ttgtacagaa tatgaatata agtgtggcaa tgggcattgc    11820
attccacatg acaatgtgtg tgatgatgcc gatgactgtg gtgactggtc cgatgaactg    11880
ggttgcaata aggaaaaga aagaacatgt gctgaaaata tatgcgagca aaattgtacc    11940
caattaaatg aaggaggatt tatctgctcc tgtacagctg ggttcgaaac caatgttttt    12000
gacagaacct cctgtctaga tatcaatgaa tgtgaacaat ttgggacttg tccccagcac    12060
tgcagaaata ccaaaggaag ttatgagtgt gtctgtgctg atggcttcac gtctatgagt    12120
gaccgccctg gaaaacgatg tgcagctgag ggtagctctc ctttgttgct actgcctgac    12180
aatgtccgaa ttcgaaaata taatctctca tctgagaggt tctcagagta tcttcaagat    12240
gaggaatata tccaagctgt tgattatgat tgggatccca aggacatagg cctcagtgtt    12300
gtgtattaca ctgtgcgagg ggagggctct aggtttggtg ctatcaaacg tgcctacatc    12360
cccaactttg aatccggccg caataatctt gtgcaggaag ttgacctgaa actgaaatac    12420
gtaatgcagc cagatggaat agcagtggac tgggttggaa ggcatattta ctggtcagat    12480
gtcaagaata aacgcattga ggtggctaaa cttgatggaa ggtacagaaa gtggctgatt    12540
tccactgacc tggaccaacc agctgctatt gctgtgaatc ccaaactagg gcttatgttc    12600
tggactgact ggggaaagga acctaaaatc gagtctgcct ggatgaatgg agaggaccgc    12660
aacatcctgg ttttcgagga ccttggttgg ccaactggcc tttctatcga ttatttgaac    12720
aatgaccgaa tctactggag tgacttcaag gaggacgtta ttgaaaccat aaaatatgat    12780
gggactgata ggagagtcat tgcaaaggaa gcaatgaacc cttacagcct ggacatcttt    12840
gaagaccagt tatactggat atctaaggaa aagggagaag tatggaaaca aaataaattt    12900
gggcaaggaa agaaagagaa aacgctggta gtgaaccctt ggctcactca agttcgaatc    12960
tttcatcaac tcagatacaa taagtcagtg cccaaccttt gcaaacagat ctgcagccac    13020
ctctgccttc tgagacctgg aggatacagc tgtgcctgtc cccaaggctc cagctttata    13080
gaggggagca ccactgagtg tgatgcagcc atcgaactgc ctatcaacct gccccccca    13140 tgcaggtgca tgcacggagg aaattgctat tttgatgaga ctgacctccc caaatgcaag    13200
tgtcctagcg gctacaccgg aaaatattgt gaaatggcgt tttcaaaagg catctctcca    13260
ggaacaaccg cagtagctgt gctgttgaca atcctcttga tcgtcgtaat tggagctctg    13320
gcaattgcag gattcttcca ctatagaagg accggctccc ttttgcctgc tctgcccaag    13380
ctgccaagct taagcagtct cgtcaagccc tctgaaaatg ggaatggggt gaccttcaga    13440
tcaggggcag atcttaacat ggatattgga gtgtctggtt ttggacctga gactgctatt    13500
gacaggtcaa tggcaatgag tgaagacttt gtcatggaaa tggggaagca gcccataata    13560
tttgaaaacc caatgtactc agccagagac agtgctgtca agtggttca gccaatccag    13620 gtgactgtat ctgaaaatgt ggataataag aattatggaa gtcccataaa cccttctgag    13680
atagttccag agacaaaccc aacttccacca gctgctgatg aactcaggt gacaaaatgg    13740 aatctcttca aacgaaaatc taaacaaact accaactttg aaaatccaat ctatgcacag    13800
atggagaacg agcaaaagga aagtgttgct gcgacaccac ctccatcacc ttcgctccct    13860
gctaagccta agcctccttc gagaagagac ccaactccaa cctattctgc aacagaagac    13920
acttttaaag acaccgcaaa tcttgttaaa gaagactctg aagtatag          13968

<210> SEQ ID NO 2
```

<211> LENGTH: 4655
<212> TYPE: PRT
<213> ORGANISM: Homo sapiens

<400> SEQUENCE: 2

```
Met Asp Arg Gly Pro Ala Ala Val Ala Cys Thr Leu Leu Ala Leu
 1               5                  10                  15

Val Ala Cys Leu Ala Pro Ala Ser Gly Gln Glu Cys Asp Ser Ala His
             20                  25                  30

Phe Arg Cys Gly Ser Gly His Cys Ile Pro Ala Asp Trp Arg Cys Asp
             35                  40                  45

Gly Thr Lys Asp Cys Ser Asp Asp Ala Asp Glu Ile Gly Cys Ala Val
     50                  55                  60

Val Thr Cys Gln Gln Gly Tyr Phe Lys Cys Gln Ser Glu Gly Gln Cys
 65                  70                  75                  80

Ile Pro Ser Ser Trp Val Cys Asp Gln Asp Gln Asp Cys Asp Asp Gly
                 85                  90                  95

Ser Asp Glu Arg Gln Asp Cys Ser Gln Ser Thr Cys Ser Ser His Gln
                100                 105                 110

Ile Thr Cys Ser Asn Gly Gln Cys Ile Pro Ser Glu Tyr Arg Cys Asp
                115                 120                 125

His Val Arg Asp Cys Pro Asp Gly Ala Asp Glu Asn Asp Cys Gln Tyr
        130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
                180                 185                 190

Gly Glu Cys Ile Pro Arg Ala Tyr Val Cys Asp His Asp Asn Asp Cys
                195                 200                 205

Gln Asp Gly Ser Asp Glu His Ala Cys Asn Tyr Pro Thr Cys Gly Gly
        210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
                260                 265                 270

Cys Pro Glu Ser Gly Arg Cys Ile Ser Ile Tyr Lys Val Cys Asp Gly
                275                 280                 285

Ile Leu Asp Cys Pro Gly Arg Glu Asp Glu Asn Asn Thr Ser Thr Gly
        290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
                340                 345                 350

Gln Ile Trp Gly Ile Cys Asp Gln Lys Cys Glu Ser Arg Pro Gly Arg
                355                 360                 365

His Leu Cys His Cys Glu Glu Gly Tyr Ile Leu Glu Arg Gly Gln Tyr
        370                 375                 380

Cys Lys Ala Asn Asp Ser Phe Gly Glu Ala Ser Ile Ile Phe Ser Asn
385                 390                 395                 400
```

```
Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
            420                 425                 430

Tyr His Leu Gln Arg Val Phe Trp Thr Asp Thr Val Gln Asn Lys Val
        435                 440                 445

Phe Ser Val Asp Ile Asn Gly Leu Asn Ile Gln Glu Val Leu Asn Val
    450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
            500                 505                 510

Arg Gly Ile Ala Val Asp Pro Thr Val Gly Tyr Leu Phe Phe Ser Asp
        515                 520                 525

Trp Glu Ser Leu Ser Gly Glu Pro Lys Leu Glu Arg Ala Phe Met Asp
    530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
            580                 585                 590

Thr Val Val His Gly Gly Ser Leu Ile Pro His Pro Phe Gly Val Ser
        595                 600                 605

Leu Phe Glu Gly Gln Val Phe Phe Thr Asp Trp Thr Lys Met Ala Val
    610                 615                 620

Leu Lys Ala Asn Lys Phe Thr Glu Thr Asn Pro Gln Val Tyr Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
            660                 665                 670

Val Cys Val Leu Ser His Arg Thr Asp Asn Asp Gly Leu Gly Phe Arg
        675                 680                 685

Cys Lys Cys Thr Phe Gly Phe Gln Leu Asp Thr Asp Glu Arg His Cys
    690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
            740                 745                 750

Ser Thr Ile Phe Phe Ser Asp Met Ser Lys His Met Ile Phe Lys Gln
        755                 760                 765

Lys Ile Asp Gly Thr Gly Arg Glu Ile Leu Ala Ala Asn Arg Val Glu
    770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
```

```
                820                 825                 830
Val His Pro Phe Ala Gly Tyr Leu Phe Phe Thr Asp Trp Phe Arg Pro
            835                 840                 845
Ala Lys Ile Met Arg Ala Trp Ser Asp Gly Ser His Leu Leu Pro Val
        850                 855                 860
Ile Asn Thr Thr Leu Gly Trp Pro Asn Gly Leu Ala Ile Asp Trp Ala
865                 870                 875                 880
Ala Ser Arg Leu Tyr Trp Val Asp Ala Tyr Phe Asp Lys Ile Glu His
                885                 890                 895
Ser Thr Phe Asp Gly Leu Asp Arg Arg Leu Gly His Ile Glu Gln
            900                 905                 910
Met Thr His Pro Phe Gly Leu Ala Ile Phe Gly Glu His Leu Phe Phe
        915                 920                 925
Thr Asp Trp Arg Leu Gly Ala Ile Ile Arg Val Arg Lys Ala Asp Gly
            930                 935                 940
Gly Glu Met Thr Val Ile Arg Ser Gly Ile Ala Tyr Ile Leu His Leu
945                 950                 955                 960
Lys Ser Tyr Asp Val Asn Ile Gln Thr Gly Ser Asn Ala Cys Asn Gln
                965                 970                 975
Pro Thr His Pro Asn Gly Asp Cys Ser His Phe Cys Phe Pro Val Pro
            980                 985                 990
Asn Phe Gln Arg Val Cys Gly Cys Pro Tyr Gly Met Arg Leu Ala Ser
                995                1000                1005
Asn His Leu Thr Cys Glu Gly Asp Pro Thr Asn Glu Pro Pro Thr Glu
        1010                1015                1020
Gln Cys Gly Leu Phe Ser Phe Pro Cys Lys Asn Gly Arg Cys Val Pro
1025                1030                1035                1040
Asn Tyr Tyr Leu Cys Asp Gly Val Asp Asp Cys His Asp Asn Ser Asp
                1045                1050                1055
Glu Gln Leu Cys Gly Thr Leu Asn Asn Thr Cys Ser Ser Ser Ala Phe
            1060                1065                1070
Thr Cys Gly His Gly Glu Cys Ile Pro Ala His Trp Arg Cys Asp Lys
        1075                1080                1085
Arg Asn Asp Cys Val Asp Gly Ser Asp Glu His Asn Cys Pro Thr His
        1090                1095                1100
Ala Pro Ala Ser Cys Leu Asp Thr Gln Tyr Thr Cys Asp Asn His Gln
1105                1110                1115                1120
Cys Ile Ser Lys Asn Trp Val Cys Asp Thr Asp Asn Asp Cys Gly Asp
            1125                1130                1135
Gly Ser Asp Glu Lys Asn Cys Asn Ser Thr Glu Thr Cys Gln Pro Ser
        1140                1145                1150
Gln Phe Asn Cys Pro Asn His Arg Cys Ile Asp Leu Ser Phe Val Cys
            1155                1160                1165
Asp Gly Asp Lys Asp Cys Val Asp Gly Ser Asp Glu Val Gly Cys Val
            1170                1175                1180
Leu Asn Cys Thr Ala Ser Gln Phe Lys Cys Ala Ser Gly Asp Lys Cys
1185                1190                1195                1200
Ile Gly Val Thr Asn Arg Cys Asp Gly Val Phe Asp Cys Ser Asp Asn
            1205                1210                1215
Ser Asp Glu Ala Gly Cys Pro Thr Arg Pro Pro Gly Met Cys His Ser
            1220                1225                1230
Asp Glu Phe Gln Cys Gln Glu Asp Gly Ile Cys Ile Pro Asn Phe Trp
            1235                1240                1245
```

-continued

```
Glu Cys Asp Gly His Pro Asp Cys Leu Tyr Gly Ser Asp Glu His Asn
1250                1255                1260

Ala Cys Val Pro Lys Thr Cys Pro Ser Ser Tyr Phe His Cys Asp Asn
1265                1270                1275                1280

Gly Asn Cys Ile His Arg Ala Trp Leu Cys Asp Arg Asp Asn Asp Cys
            1285                1290                1295

Gly Asp Met Ser Asp Glu Lys Asp Cys Pro Thr Gln Pro Phe Arg Cys
        1300                1305                1310

Pro Ser Trp Gln Trp Gln Cys Leu Gly His Asn Ile Cys Val Asn Leu
    1315                1320                1325

Ser Val Val Cys Asp Gly Ile Phe Asp Cys Pro Asn Gly Thr Asp Glu
1330                1335                1340

Ser Pro Leu Cys Asn Gly Asn Ser Cys Ser Asp Phe Asn Gly Gly Cys
1345                1350                1355                1360

Thr His Glu Cys Val Gln Glu Pro Phe Gly Ala Lys Cys Leu Cys Pro
            1365                1370                1375

Leu Gly Phe Leu Leu Ala Asn Asp Ser Lys Thr Cys Glu Asp Ile Asp
        1380                1385                1390

Glu Cys Asp Ile Leu Gly Ser Cys Ser Gln His Cys Tyr Asn Met Arg
    1395                1400                1405

Gly Ser Phe Arg Cys Ser Cys Asp Thr Gly Tyr Met Leu Glu Ser Asp
1410                1415                1420

Gly Arg Thr Cys Lys Val Thr Ala Ser Glu Ser Leu Leu Leu Leu Val
1425                1430                1435                1440

Ala Ser Gln Asn Lys Ile Ile Ala Asp Ser Val Thr Ser Gln Val His
            1445                1450                1455

Asn Ile Tyr Ser Leu Val Glu Asn Gly Ser Tyr Ile Val Ala Val Asp
        1460                1465                1470

Phe Asp Ser Ile Ser Gly Arg Ile Phe Trp Ser Asp Ala Thr Gln Gly
    1475                1480                1485

Lys Thr Trp Ser Ala Phe Gln Asn Gly Thr Asp Arg Arg Val Val Phe
1490                1495                1500

Asp Ser Ser Ile Ile Leu Thr Glu Thr Ile Ala Ile Asp Trp Val Gly
1505                1510                1515                1520

Arg Asn Leu Tyr Trp Thr Asp Tyr Ala Leu Glu Thr Ile Glu Val Ser
            1525                1530                1535

Lys Ile Asp Gly Ser His Arg Thr Val Leu Ile Ser Lys Asn Leu Thr
        1540                1545                1550

Asn Pro Arg Gly Leu Ala Leu Asp Pro Arg Met Asn Glu His Leu Leu
    1555                1560                1565

Phe Trp Ser Asp Trp Gly His His Pro Arg Ile Glu Arg Ala Ser Met
    1570                1575                1580

Asp Gly Ser Met Arg Thr Val Ile Val Gln Asp Lys Ile Phe Trp Pro
1585                1590                1595                1600

Cys Gly Leu Thr Ile Asp Tyr Pro Asn Arg Leu Leu Tyr Phe Met Asp
            1605                1610                1615

Ser Tyr Leu Asp Tyr Met Asp Phe Cys Asp Tyr Asn Gly His His Arg
        1620                1625                1630

Arg Gln Val Ile Ala Ser Asp Leu Ile Ile Arg His Pro Tyr Ala Leu
    1635                1640                1645

Thr Leu Phe Glu Asp Ser Val Tyr Trp Thr Asp Arg Ala Thr Arg Arg
    1650                1655                1660

Val Met Arg Ala Asn Lys Trp His Gly Gly Asn Gln Ser Val Val Met
1665                1670                1675                1680
```

```
Tyr Asn Ile Gln Trp Pro Leu Gly Ile Val Ala Val His Pro Ser Lys
            1685                1690                1695

Gln Pro Asn Ser Val Asn Pro Cys Ala Phe Ser Arg Cys Ser His Leu
        1700                1705                1710

Cys Leu Leu Ser Ser Gln Gly Pro His Phe Tyr Ser Cys Val Cys Pro
    1715                1720                1725

Ser Gly Trp Ser Leu Ser Pro Asp Leu Leu Asn Cys Leu Arg Asp Asp
1730                1735                1740

Gln Pro Phe Leu Ile Thr Val Arg Gln His Ile Ile Phe Gly Ile Ser
1745                1750                1755                1760

Leu Asn Pro Glu Val Lys Ser Asn Asp Ala Met Val Pro Ile Ala Gly
            1765                1770                1775

Ile Gln Asn Gly Leu Asp Val Glu Phe Asp Asp Ala Glu Gln Tyr Ile
        1780                1785                1790

Tyr Trp Val Glu Asn Pro Gly Glu Ile His Arg Val Lys Thr Asp Gly
    1795                1800                1805

Thr Asn Arg Thr Val Phe Ala Ser Ile Ser Met Val Gly Pro Ser Met
1810                1815                1820

Asn Leu Ala Leu Asp Trp Ile Ser Arg Asn Leu Tyr Ser Thr Asn Pro
1825                1830                1835                1840

Arg Thr Gln Ser Ile Glu Val Leu Thr Leu His Gly Asp Ile Arg Tyr
            1845                1850                1855

Arg Lys Thr Leu Ile Ala Asn Asp Gly Thr Ala Leu Gly Val Gly Phe
        1860                1865                1870

Pro Ile Gly Ile Thr Val Asp Pro Ala Arg Gly Lys Leu Tyr Trp Ser
    1875                1880                1885

Asp Gln Gly Thr Asp Ser Gly Val Pro Ala Lys Ile Ala Ser Ala Asn
1890                1895                1900

Met Asp Gly Thr Ser Val Lys Thr Leu Phe Thr Gly Asn Leu Glu His
1905                1910                1915                1920

Leu Glu Cys Val Thr Leu Asp Ile Glu Glu Gln Lys Leu Tyr Trp Ala
            1925                1930                1935

Val Thr Gly Arg Gly Val Ile Glu Arg Gly Asn Val Asp Gly Thr Asp
        1940                1945                1950

Arg Met Ile Leu Val His Gln Leu Ser His Pro Trp Gly Ile Ala Val
    1955                1960                1965

His Asp Ser Phe Leu Tyr Tyr Thr Asp Glu Gln Tyr Glu Val Ile Glu
1970                1975                1980

Arg Val Asp Lys Ala Thr Gly Ala Asn Lys Ile Val Leu Arg Asp Asn
1985                1990                1995                2000

Val Pro Asn Leu Arg Gly Leu Gln Val Tyr His Arg Arg Asn Ala Ala
            2005                2010                2015

Glu Ser Ser Asn Gly Cys Ser Asn Asn Met Asn Ala Cys Gln Gln Ile
        2020                2025                2030

Cys Leu Pro Val Pro Gly Gly Leu Phe Ser Cys Ala Cys Ala Thr Gly
    2035                2040                2045

Phe Lys Leu Asn Pro Asp Asn Arg Ser Cys Ser Pro Tyr Asn Ser Phe
2050                2055                2060

Ile Val Val Ser Met Leu Ser Ala Ile Arg Gly Phe Ser Leu Glu Leu
2065                2070                2075                2080

Ser Asp His Ser Glu Thr Met Val Pro Val Ala Gly Gln Gly Arg Asn
            2085                2090                2095

Ala Leu His Val Asp Val Asp Val Ser Ser Gly Phe Ile Tyr Trp Cys
```

-continued

Asp Phe Ser Ser Ser Val Ala Ser Asp Asn Ala Ile Arg Arg Ile Lys
 2100                2105                2110

Pro Asp Gly Ser Ser Leu Met Asn Ile Val Thr His Gly Ile Gly Glu
 2115                2120                2125

Asn Gly Val Arg Gly Ile Ala Val Asp Trp Val Ala Gly Asn Leu Tyr
 2130                2135                2140

Phe Thr Asn Ala Phe Val Ser Glu Thr Leu Ile Glu Val Leu Arg Ile
 2145                2150                2155                2160

Asn Thr Thr Tyr Arg Arg Val Leu Leu Lys Val Thr Val Asp Met Pro
 2165                2170                2175

Arg His Ile Val Val Asp Pro Lys Asn Arg Tyr Leu Phe Trp Ala Asp
 2180                2185                2190

Tyr Gly Gln Arg Pro Lys Ile Glu Arg Ser Phe Leu Asp Cys Thr Asn
 2195                2200                2205

Arg Thr Val Leu Val Ser Glu Gly Ile Val Thr Pro Arg Gly Leu Ala
2210                2215                2220

Val Asp Arg Ser Asp Gly Tyr Val Tyr Trp Val Asp Asp Ser Leu Asp
 2225                2230                2235                2240

Ile Ile Ala Arg Ile Arg Ile Asn Gly Glu Asn Ser Glu Val Ile Arg
 2245                2250                2255

Tyr Gly Ser Arg Tyr Pro Thr Pro Tyr Gly Ile Thr Val Phe Glu Asn
 2260                2265                2270

Ser Ile Ile Trp Val Asp Arg Asn Leu Lys Lys Ile Phe Gln Ala Ser
 2275                2280                2285

Lys Glu Pro Glu Asn Thr Glu Pro Pro Thr Val Ile Arg Asp Asn Ile
2290                2295                2300

Asn Trp Leu Arg Asp Val Thr Ile Phe Asp Lys Gln Val Gln Pro Arg
 2305                2310                2315                2320

Ser Pro Ala Glu Val Asn Asn Asn Pro Cys Leu Glu Asn Asn Gly Gly
 2325                2330                2335

Cys Ser His Leu Cys Phe Ala Leu Pro Gly Leu His Thr Pro Lys Cys
 2340                2345                2350

Asp Cys Ala Phe Gly Thr Leu Gln Ser Asp Gly Lys Asn Cys Ala Ile
 2355                2360                2365

Ser Thr Glu Asn Phe Leu Ile Phe Ala Leu Ser Asn Ser Leu Arg Ser
2370                2375                2380

Leu His Leu Asp Pro Glu Asn His Ser Pro Pro Phe Gln Thr Ile Asn
 2385                2390                2395                2400

Val Glu Arg Thr Val Met Ser Leu Asp Tyr Asp Ser Val Ser Asp Arg
 2405                2410                2415

Ile Tyr Phe Thr Gln Asn Leu Ala Ser Gly Val Gly Gln Ile Ser Tyr
 2420                2425                2430

Ala Thr Leu Ser Ser Gly Ile His Thr Pro Thr Val Ile Ala Ser Gly
 2435                2440                2445

Ile Gly Thr Ala Asp Gly Ile Ala Phe Asp Trp Ile Thr Arg Arg Ile
2450                2455                2460

Tyr Tyr Ser Asp Tyr Leu Asn Gln Met Ile Asn Ser Met Ala Glu Asp
 2465                2470                2475

Gly Ser Asn Arg Thr Val Ile Ala Arg Val Pro Lys Pro Arg Ala Ile
 2480                2485                2490

Val Leu Asp Pro Cys Gln Gly Tyr Leu Tyr Trp Ala Asp Trp Asp Thr
 2495                2500                2505

-continued

```
His Ala Lys Ile Glu Arg Ala Thr Leu Gly Gly Asn Phe Arg Val Pro
    2530                2535                2540

Ile Val Asn Ser Ser Leu Val Met Pro Ser Gly Leu Thr Leu Asp Tyr
2545                2550                2555                2560

Glu Glu Asp Leu Leu Tyr Trp Val Asp Ala Ser Leu Gln Arg Ile Glu
                2565                2570                2575

Arg Ser Thr Leu Thr Gly Val Asp Arg Glu Val Ile Val Asn Ala Ala
            2580                2585                2590

Val His Ala Phe Gly Leu Thr Leu Tyr Gly Gln Tyr Ile Tyr Trp Thr
        2595                2600                2605

Asp Leu Tyr Thr Gln Arg Ile Tyr Arg Ala Asn Lys Tyr Asp Gly Ser
    2610                2615                2620

Gly Gln Ile Ala Met Thr Thr Asn Leu Leu Ser Gln Pro Arg Gly Ile
2625                2630                2635                2640

Asn Thr Val Val Lys Asn Gln Lys Gln Gln Cys Asn Asn Pro Cys Glu
                2645                2650                2655

Gln Phe Asn Gly Gly Cys Ser His Ile Cys Ala Pro Gly Pro Asn Gly
            2660                2665                2670

Ala Glu Cys Gln Cys Pro His Glu Gly Asn Trp Tyr Leu Ala Asn Asn
        2675                2680                2685

Arg Lys His Cys Ile Val Asp Asn Gly Glu Arg Cys Gly Ala Ser Ser
    2690                2695                2700

Phe Thr Cys Ser Asn Gly Arg Cys Ile Ser Glu Glu Trp Lys Cys Asp
2705                2710                2715                2720

Asn Asp Asn Asp Cys Gly Asp Gly Ser Asp Glu Met Glu Ser Val Cys
                2725                2730                2735

Ala Leu His Thr Cys Ser Pro Thr Ala Phe Thr Cys Ala Asn Gly Arg
            2740                2745                2750

Cys Val Gln Tyr Ser Tyr Arg Cys Asp Tyr Tyr Asn Asp Cys Gly Asp
        2755                2760                2765

Gly Ser Asp Glu Ala Gly Cys Leu Phe Arg Asp Cys Asn Ala Thr Thr
    2770                2775                2780

Glu Phe Met Cys Asn Asn Arg Arg Cys Ile Pro Arg Glu Phe Ile Cys
2785                2790                2795                2800

Asn Gly Val Asp Asn Cys His Asp Asn Asn Thr Ser Asp Glu Lys Asn
                2805                2810                2815

Cys Pro Asp Arg Thr Cys Gln Ser Gly Tyr Thr Lys Cys His Asn Ser
            2820                2825                2830

Asn Ile Cys Ile Pro Arg Val Tyr Leu Cys Asp Gly Asp Asn Asp Cys
        2835                2840                2845

Gly Asp Asn Ser Asp Glu Asn Pro Thr Tyr Cys Thr Thr His Thr Cys
    2850                2855                2860

Ser Ser Ser Glu Phe Gln Cys Ala Ser Gly Arg Cys Ile Pro Gln His
2865                2870                2875                2880

Trp Tyr Cys Asp Gln Glu Thr Asp Cys Phe Asp Ala Ser Asp Glu Pro
                2885                2890                2895

Ala Ser Cys Gly His Ser Glu Arg Thr Cys Leu Ala Asp Glu Phe Lys
            2900                2905                2910

Cys Asp Gly Gly Arg Cys Ile Pro Ser Glu Trp Ile Cys Asp Gly Asp
        2915                2920                2925

Asn Asp Cys Gly Asp Met Ser Asp Glu Asp Lys Arg His Gln Cys Gln
    2930                2935                2940

Asn Gln Asn Cys Ser Asp Ser Glu Phe Leu Cys Val Asn Asp Arg Pro
2945                2950                2955                2960
```

```
Pro Asp Arg Arg Cys Ile Pro Gln Ser Trp Val Cys Asp Gly Asp Val
            2965                2970                2975

Asp Cys Thr Asp Gly Tyr Asp Glu Asn Gln Asn Cys Thr Arg Arg Thr
            2980                2985                2990

Cys Ser Glu Asn Glu Phe Thr Cys Gly Tyr Gly Leu Cys Ile Pro Lys
            2995                3000                3005

Ile Phe Arg Cys Asp Arg His Asn Asp Cys Gly Asp Tyr Ser Asp Glu
            3010                3015                3020

Arg Gly Cys Leu Tyr Gln Thr Cys Gln Gln Asn Gln Phe Thr Cys Gln
3025                3030                3035                3040

Asn Gly Arg Cys Ile Ser Lys Thr Phe Val Cys Asp Glu Asp Asn Asp
            3045                3050                3055

Cys Gly Asp Gly Ser Asp Glu Leu Met His Leu Cys His Thr Pro Glu
            3060                3065                3070

Pro Thr Cys Pro Pro His Glu Phe Lys Cys Asp Asn Gly Arg Cys Ile
            3075                3080                3085

Glu Met Met Lys Leu Cys Asn His Leu Asp Asp Cys Leu Asp Asn Ser
            3090                3095                3100

Asp Glu Lys Gly Cys Gly Ile Asn Glu Cys His Asp Pro Ser Ile Ser
3105                3110                3115                3120

Gly Cys Asp His Asn Cys Thr Asp Thr Leu Thr Ser Phe Tyr Cys Ser
            3125                3130                3135

Cys Arg Pro Gly Tyr Lys Leu Met Ser Asp Lys Arg Thr Cys Val Asp
            3140                3145                3150

Ile Asp Glu Cys Thr Glu Met Pro Phe Val Cys Ser Gln Lys Cys Glu
            3155                3160                3165

Asn Val Ile Gly Ser Tyr Ile Cys Lys Cys Ala Pro Gly Tyr Leu Arg
            3170                3175                3180

Glu Pro Asp Gly Lys Thr Cys Arg Gln Asn Ser Asn Ile Glu Pro Tyr
3185                3190                3195                3200

Leu Ile Phe Ser Asn Arg Tyr Tyr Leu Arg Asn Leu Thr Ile Asp Gly
            3205                3210                3215

Tyr Phe Tyr Ser Leu Ile Leu Glu Gly Leu Asp Asn Val Val Ala Leu
            3220                3225                3230

Asp Phe Asp Arg Val Glu Lys Arg Leu Tyr Trp Ile Asp Thr Gln Arg
            3235                3240                3245

Gln Val Ile Glu Arg Met Phe Leu Asn Lys Thr Asn Lys Glu Thr Ile
3250                3255                3260

Ile Asn His Arg Leu Pro Ala Ala Glu Ser Leu Ala Val Asp Trp Val
3265                3270                3275                3280

Ser Arg Lys Leu Tyr Trp Leu Asp Ala Arg Leu Asp Gly Leu Phe Val
            3285                3290                3295

Ser Asp Leu Asn Gly Gly His Arg Arg Met Leu Ala Gln His Cys Val
            3300                3305                3310

Asp Ala Asn Asn Thr Phe Cys Phe Asp Asn Pro Arg Gly Leu Ala Leu
            3315                3320                3325

His Pro Gln Tyr Gly Tyr Leu Tyr Trp Ala Asp Trp Gly His Arg Ala
            3330                3335                3340

Tyr Ile Gly Arg Val Gly Met Asp Gly Thr Asn Lys Ser Val Ile Ile
3345                3350                3355                3360

Ser Thr Lys Leu Glu Trp Pro Asn Gly Ile Thr Ile Asp Tyr Thr Asn
            3365                3370                3375

Asp Leu Leu Tyr Trp Ala Asp Ala His Leu Gly Tyr Ile Glu Tyr Ser
```

-continued

```
                 3380                3385                3390
Asp Leu Glu Gly His His Arg His Thr Val Tyr Asp Gly Ala Leu Pro
            3395                3400                3405
His Pro Phe Ala Ile Thr Ile Phe Glu Asp Thr Ile Tyr Trp Thr Asp
        3410                3415                3420
Trp Asn Thr Arg Thr Val Glu Lys Gly Asn Lys Tyr Asp Gly Ser Asn
3425                3430                3435                3440
Arg Gln Thr Leu Val Asn Thr Thr His Arg Pro Phe Asp Ile His Val
                3445                3450                3455
Tyr His Pro Tyr Arg Gln Pro Ile Val Ser Asn Pro Cys Gly Thr Asn
            3460                3465                3470
Asn Gly Gly Cys Ser His Leu Cys Leu Ile Lys Pro Gly Lys Gly
        3475                3480                3485
Phe Thr Cys Glu Cys Pro Asp Asp Phe Arg Thr Leu Gln Leu Ser Gly
    3490                3495                3500
Ser Thr Tyr Cys Met Pro Met Cys Ser Ser Thr Gln Phe Leu Cys Ala
3505                3510                3515                3520
Asn Asn Glu Lys Cys Ile Pro Ile Trp Trp Lys Cys Asp Gly Gln Lys
                3525                3530                3535
Asp Cys Ser Asp Gly Ser Asp Glu Leu Ala Leu Cys Pro Gln Arg Phe
            3540                3545                3550
Cys Arg Leu Gly Gln Phe Gln Cys Ser Asp Gly Asn Cys Thr Ser Pro
        3555                3560                3565
Gln Thr Leu Cys Asn Ala His Gln Asn Cys Pro Asp Gly Ser Asp Glu
    3570                3575                3580
Asp Arg Leu Leu Cys Glu Asn His His Cys Asp Ser Asn Glu Trp Gln
3585                3590                3595                3600
Cys Ala Asn Lys Arg Cys Ile Pro Glu Ser Trp Gln Cys Asp Thr Phe
                3605                3610                3615
Asn Asp Cys Glu Asp Asn Ser Asp Glu Asp Ser Ser His Cys Ala Ser
            3620                3625                3630
Arg Thr Cys Arg Pro Gly Gln Phe Arg Cys Ala Asn Gly Arg Cys Ile
        3635                3640                3645
Pro Gln Ala Trp Lys Cys Asp Val Asp Asn Asp Cys Gly Asp His Ser
    3650                3655                3660
Asp Glu Pro Ile Glu Glu Cys Met Ser Ser Ala His Leu Cys Asp Asn
3665                3670                3675                3680
Phe Thr Glu Phe Ser Cys Lys Thr Asn Tyr Arg Cys Ile Pro Lys Trp
                3685                3690                3695
Ala Val Cys Asn Gly Val Asp Asp Cys Arg Asp Asn Ser Asp Glu Gln
            3700                3705                3710
Gly Cys Glu Glu Arg Thr Cys His Pro Val Gly Asp Phe Arg Cys Lys
        3715                3720                3725
Asn His His Cys Ile Pro Leu Arg Trp Gln Cys Asp Gly Gln Asn Asp
    3730                3735                3740
Cys Gly Asp Asn Ser Asp Glu Glu Asn Cys Ala Pro Arg Glu Cys Thr
3745                3750                3755                3760
Glu Ser Glu Phe Arg Cys Val Asn Gln Gln Cys Ile Pro Ser Arg Trp
                3765                3770                3775
Ile Cys Asp His Tyr Asn Asp Cys Gly Asp Asn Ser Asp Glu Arg Asp
            3780                3785                3790
Cys Glu Met Arg Thr Cys His Pro Glu Tyr Phe Gln Cys Thr Ser Gly
        3795                3800                3805
```

```
His Cys Val His Ser Glu Leu Lys Cys Asp Gly Ser Ala Asp Cys Leu
    3810                3815                3820

Asp Ala Ser Asp Glu Ala Asp Cys Pro Thr Arg Phe Pro Asp Gly Ala
3825                3830                3835                3840

Tyr Cys Gln Ala Thr Met Phe Glu Cys Lys Asn His Val Cys Ile Pro
            3845                3850                3855

Pro Tyr Trp Lys Cys Asp Gly Asp Asp Cys Gly Asp Gly Ser Asp
        3860                3865                3870

Glu Glu Leu His Leu Cys Leu Asp Val Pro Cys Asn Ser Pro Asn Arg
        3875                3880                3885

Phe Arg Cys Asp Asn Asn Arg Cys Ile Tyr Ser His Glu Val Cys Asn
    3890                3895                3900

Gly Val Asp Asp Cys Gly Asp Gly Thr Asp Glu Thr Glu Glu His Cys
3905                3910                3915                3920

Arg Lys Pro Thr Pro Lys Pro Cys Thr Glu Tyr Glu Tyr Lys Cys Gly
            3925                3930                3935

Asn Gly His Cys Ile Pro His Asp Asn Val Cys Asp Ala Asp Asp
        3940                3945                3950

Cys Gly Asp Trp Ser Asp Glu Leu Gly Cys Asn Lys Gly Lys Glu Arg
    3955                3960                3965

Thr Cys Ala Glu Asn Ile Cys Glu Gln Asn Cys Thr Gln Leu Asn Glu
        3970                3975                3980

Gly Gly Phe Ile Cys Ser Cys Thr Ala Gly Phe Glu Thr Asn Val Phe
3985                3990                3995                4000

Asp Arg Thr Ser Cys Leu Asp Ile Asn Glu Cys Glu Gln Phe Gly Thr
            4005                4010                4015

Cys Pro Gln His Cys Arg Asn Thr Lys Gly Ser Tyr Glu Cys Val Cys
        4020                4025                4030

Ala Asp Gly Phe Thr Ser Met Ser Asp Arg Pro Gly Lys Arg Cys Ala
        4035                4040                4045

Ala Glu Gly Ser Ser Pro Leu Leu Leu Leu Pro Asp Asn Val Arg Ile
    4050                4055                4060

Arg Lys Tyr Asn Leu Ser Ser Glu Arg Phe Ser Glu Tyr Leu Gln Asp
4065                4070                4075                4080

Glu Glu Tyr Ile Gln Ala Val Asp Tyr Asp Trp Asp Pro Lys Asp Ile
            4085                4090                4095

Gly Leu Ser Val Val Tyr Tyr Thr Val Arg Gly Glu Gly Ser Arg Phe
        4100                4105                4110

Gly Ala Ile Lys Arg Ala Tyr Ile Pro Asn Phe Glu Ser Gly Arg Asn
        4115                4120                4125

Asn Leu Val Gln Glu Val Asp Leu Lys Leu Lys Tyr Val Met Gln Pro
    4130                4135                4140

Asp Gly Ile Ala Val Asp Trp Val Gly Arg His Ile Tyr Trp Ser Asp
4145                4150                4155                4160

Val Lys Asn Lys Arg Ile Glu Val Ala Lys Leu Asp Gly Arg Tyr Arg
            4165                4170                4175

Lys Trp Leu Ile Ser Thr Asp Leu Asp Gln Pro Ala Ala Ile Ala Val
        4180                4185                4190

Asn Pro Lys Leu Gly Leu Met Phe Trp Thr Asp Trp Gly Lys Glu Pro
    4195                4200                4205

Lys Ile Glu Ser Ala Trp Met Asn Gly Glu Asp Arg Asn Ile Leu Val
    4210                4215                4220

Phe Glu Asp Leu Gly Trp Pro Thr Gly Leu Ser Ile Asp Tyr Leu Asn
4225                4230                4235                4240
```

```
Asn Asp Arg Ile Tyr Trp Ser Asp Phe Lys Glu Asp Val Ile Glu Thr
            4245                4250                4255
Ile Lys Tyr Asp Gly Thr Asp Arg Arg Val Ile Ala Lys Glu Ala Met
        4260                4265                4270
Asn Pro Tyr Ser Leu Asp Ile Phe Glu Asp Gln Leu Tyr Trp Ile Ser
    4275                4280                4285
Lys Glu Lys Gly Glu Val Trp Lys Gln Asn Lys Phe Gly Gln Gly Lys
4290                4295                4300
Lys Glu Lys Thr Leu Val Val Asn Pro Trp Leu Thr Gln Val Arg Ile
4305                4310                4315                4320
Phe His Gln Leu Arg Tyr Asn Lys Ser Val Pro Asn Leu Cys Lys Gln
            4325                4330                4335
Ile Cys Ser His Leu Cys Leu Leu Arg Pro Gly Gly Tyr Ser Cys Ala
            4340                4345                4350
Cys Pro Gln Gly Ser Ser Phe Ile Glu Gly Ser Thr Thr Glu Cys Asp
        4355                4360                4365
Ala Ala Ile Glu Leu Pro Ile Asn Leu Pro Pro Pro Cys Arg Cys Met
        4370                4375                4380
His Gly Gly Asn Cys Tyr Phe Asp Glu Thr Asp Leu Pro Lys Cys Lys
4385                4390                4395                4400
Cys Pro Ser Gly Tyr Thr Gly Lys Tyr Cys Glu Met Ala Phe Ser Lys
        4405                4410                4415
Gly Ile Ser Pro Gly Thr Thr Ala Val Ala Val Leu Leu Thr Ile Leu
            4420                4425                4430
Leu Ile Val Val Ile Gly Ala Leu Ala Ile Ala Gly Phe Phe His Tyr
            4435                4440                4445
Arg Arg Thr Gly Ser Leu Leu Pro Ala Leu Pro Lys Leu Pro Ser Leu
        4450                4455                4460
Ser Ser Leu Val Lys Pro Ser Glu Asn Gly Asn Gly Val Thr Phe Arg
4465                4470                4475                4480
Ser Gly Ala Asp Leu Asn Met Asp Ile Gly Val Ser Gly Phe Gly Pro
        4485                4490                4495
Glu Thr Ala Ile Asp Arg Ser Met Ala Met Ser Glu Asp Phe Val Met
            4500                4505                4510
Glu Met Gly Lys Gln Pro Ile Ile Phe Glu Asn Pro Met Tyr Ser Ala
        4515                4520                4525
Arg Asp Ser Ala Val Lys Val Val Gln Pro Ile Gln Val Thr Val Ser
        4530                4535                4540
Glu Asn Val Asp Asn Lys Asn Tyr Gly Ser Pro Ile Asn Pro Ser Glu
4545                4550                4555                4560
Ile Val Pro Glu Thr Asn Pro Thr Ser Pro Ala Ala Asp Gly Thr Gln
            4565                4570                4575
Val Thr Lys Trp Asn Leu Phe Lys Arg Lys Ser Lys Gln Thr Thr Asn
        4580                4585                4590
Phe Glu Asn Pro Ile Tyr Ala Gln Met Glu Asn Glu Gln Lys Glu Ser
        4595                4600                4605
Val Ala Ala Thr Pro Pro Pro Ser Pro Ser Leu Pro Ala Lys Pro Lys
        4610                4615                4620
Pro Pro Ser Arg Arg Asp Pro Thr Pro Thr Tyr Ser Ala Thr Glu Asp
4625                4630                4635                4640
Thr Phe Lys Asp Thr Ala Asn Leu Val Lys Glu Asp Ser Glu Val
            4645                4650                4655
```

METHOD FOR MEASURING HUMAN MEGALIN

CROSS REFERENCE TO RELATED APPLICATIONS

This application is a divisional application of U.S. Ser. No. 12/293,992 filed Sep. 22, 2008, which is the U.S. National Phase of PCT/JP2007/056660 filed Mar. 28, 2007, which claims priority from Japanese Patent Application No. 2006-089306 filed Mar. 28, 2006. The subject matter of each of the above referenced applications is incorporated in entirety by reference.

TECHNICAL FIELD

The present invention relates to a method for measuring human megalin. More particularly, the present invention relates to a method for detecting human megalin comprising quantitatively detecting megalin that is expressed topically and specifically in cells, tissues, and organs where megalin expression is observed in a rapid and simple manner, to thereby enable direct and early diagnosis of the degree to which cells, tissues, and organs are affected and improve and keep from worsening the conditions of disorders and the prognosis via treatment. The present invention can be applied to diagnosis of diseases of organs where megalin expression is observed, such as kidney or lung diseases.

BACKGROUND ART

1. Cloning of Megalin

As a result of a search for an etiologic antigen of Heymann nephritis, which is a model for experimental membranous nephropathy, Kerjaschki, D. and Farquhar, M. G. identified a cell membrane protein, gp330, in 1982 (Kerjaschki D., Farquhar M. G., 1982, Proc. Natl. Acad. Sci. U.S.A., 79, 5557-5561). In 1994, Saito, A. et al. determined the complete primary structure of a rat gp330 and designated it as megalin, because it was the largest cloned cell membrane protein of a vertebrate (Saito A. et al., 1994, Proc. Natl. Acad. Sci. U.S.A., 91, 9725-9729).

2. Megalin-Expressing Site

Megalin is also known as glycoprotein 330 (gp330) or low-density lipoprotein (LDL) receptor-related protein 2 (LRP-2). It is a glycoprotein having a molecular weight of about 600 kDa, which is expressed in kidney proximal tubule epithelial cells, other tissues and cells, such as type II alveolar cells, spermary, uterine endometrium, placenta, or inner ear epithelium, renal epithelium, germo-vitellarium, and neural ectoderm (see Christensen E. I., Willnow, T. E., 1999, J. Am. Soc. Nephrol. 10, 2224-2236; Juhlin C., Klareskog L. et al., 1990, J. Biol. Chem. 265, 8275-8279; and Zheng G, McCluskey R. T. et al., 1994, J. Histochem. Cytochem. 42, 531-542). In the kidney, megalin functions as an endocytosis receptor associated with endocytosis and reabsorption of proteins and the like in the proximal tubule prior to urinary excretion. The reabsorbed proteins and the like are then degraded by lysosomes (see Mausbach A. B., Christensen E. I., 1992, Handbook of Physiology: Renal Physiology, Windhager, editor, New York, Oxford University Press, 42-207).

3. Nucleotide Sequence of Megalin

Megalin is a glycoprotein that is the most frequently expressed on the kidney proximal tubule epithelial membrane of a mammalian animal. The cDNA-encoding sequence thereof has nucleotide identity with the human megalin cDNA sequence having gene accession number U04441 disclosed in Korenberg, J. R. et al. (1994) or the human megalin cDNA sequence having gene accession number U33837 disclosed in Hjacln, G., et al. (1996) (see Korenberg J. R. et al., 1994, Genomics 22, 88-93; and Hjalm G. et al., 1996, Eur. J. Biochem. 239, 132-137).

Also, rat megalin having homology with human megalin has been discovered by Saito et al. (1994), and the cDNA sequence thereof having gene accession number L34049 has already been disclosed (see Saito A. et al., 1994, Proc. Natl. Acad. Sci. U.S.A., 91, 9725-9729).

4. Amino Acid Sequence and Protein Structure of Megalin

Megalin is a gigantic cell membrane protein consisting of 4,655 amino acids (in the case of human megalin) and 4,660 amino acids (in the case of rat megalin). The molecular weight deduced based on the amino acid sequence is about 520 kDa, and it can be as great as about 600 kDa, when including a sugar chain (see Saito A. et al., 1994, Proc. Natl. Acad. Sci. U.S.A., 91, 9725-9729). Megalin belongs to the LDL receptor gene family, a gigantic extracellular region thereof has four functional domains, and the extracellular region is connected to a thin intracellular region through a single transmembrane region. Megalin is mainly present in a clathrin-coated pit on the glomerulus (rat) or the epithelial luminal membrane (luminal and basal membrane in the glomerular epithelial cell) of the proximal tubule, type II alveolar cell, epididymal glands, thyroid glands, accessory thyroid glands, yolk sac membrane, inner ear, small intestine, or chorioidea, and it is associated with intake of various ligands into the cells and metabolism thereof (see Farquhar M. G. et al., 1995, J. Am. Soc. Nephrol. 6, 35-47; and Christensen E. I. et al., 2002, Nat. Rev. Mol. Cell. Biol. 3, 256-266). Low-molecular-weight proteinuria, bone metabolism disorders, respiratory failure, malformation of brain, and other disorders occur in megalin-knockout mice (see Willnow T. E. et al., 1996, Proc. Natl. Acad. Sci. U.S.A., 93, 8460-8464). A megalin homolog is also present in nematodes (C. elegans), and the biological importance thereof has been suggested (see Yochem J. et al., 1993, Proc. Natl. Acad. Sci. U.S.A., 90, 4572-4576).

5. Importance of Megalin as a Cause of Nephritis

Megalin, which is a major etiologic antigen of experimental membranous nephropathy (Heymann nephritis), is an epithelial scavenger receptor, and biological and pathological roles thereof have been elucidated. Animal models have been used for a long time in order to elucidate the mechanism of human membranous nephropathy development, and rat Heymann nephritis is a model of membranous nephropathy. The analysis of Heymann nephritis has been more advanced than that of any other model. Saito A. et al. disclosed the results of analysis of the pathological epitope and the ligand-binding domain of Heymann nephritis, and they have also demonstrated the major antigen region of megalin and a functional domain of megalin that mainly contribute to binding to a ligand (see Kerjaschki D. et al., 1992, Proc. Natl. Acad. Sci. U.S.A., 89, 11179-11183; Saito A., Farquhar M. G. et al., 1996, Proc. Natl. Acad. Sci. U.S.A., 93, 8601-8605; Yamazaki H., Farquhar M. G. et al., 1998, J. Am. Soc. Nephrol. 9, 1638-1644; and Orlando R. A., Farquhar M. G. et al., 1997, Proc. Natl. Acad. Sci. U.S.A., 94, 2368-2373).

6. Various Ligands of Megalin

Megalin is expressed most abundantly on the luminal side of the proximal tubule epithelial cells in vivo. In human kidney, megalin expression is not observed at sites other than the proximal tubule epithelial cells, including at glomeruli. Megalin incorporates various ligands (e.g., a low-molecular-weight protein or drugs) that are filtered by glomeruli into cells via endocytosis, megalin transports them to lysosomes, and they reappear on the cell surface via recycling (see Farquhar M. G. et al., 1995, J. Am. Soc. Nephrol. 6, 35-47; and Christensen E. I. et al., 2002, Nat. Rev. Mol. Cell. Biol. 3, 256-266). Also, megalin is associated with transcytosis from the luminal side to the basal membrane side. Megalin is also associated with intake and metabolism of binding proteins, such as vitamins A, $B_{12}$, and D (see Christensen E. I. et al., 2002, Nat. Rev. Mol. Cell. Biol. 3, 256-266). Christensen and Willnow demonstrated that megalin mediates reabsorption of three vitamin carrier proteins, vitamin D binding proteins (DBP), retinol binding protein (RBP), and transcobalamin (TC) and vitamins associated therewith; i.e., (OH) vitamin $25D_3$, vitamin A (retinol), and vitamin $B_{12}$ (see Christensen E. I., Willnow T. E., 1999, J. Am. Soc. Nephrol. 10, 2224-2236). Saito A. et al. demonstrated that leptin, which is secreted from adipocytes and increase in the blood of obese patients, is incorporated into and metabolized by the proximal tubule epithelial cells as the megalin ligand (see Saito A., Gejyo F. et al., 2004, Endocrinology. 145, 3935-3940). The adipocytes, that is, accumulated visceral fats, result in combined pathological conditions, i.e., metabolic syndrome. Leptin, which is an adipocytokine secreted from adipocytes, increases in the blood of a metabolic syndrome patient. It is suggested that the kidney is the organ in which leptin in the blood is most likely to accumulate and that leptin plays a nephropathic role (see Tarzi R. M. Lord G. M. et al., 2004, Am. J. Pathol. 164, 385-390). A so-called leptin receptor is also found in a region between the proximal tubule and the collecting tubule located downstream of the megalin functioning region.

The term "metabolic syndrome" is defined as a disease complication of visceral obesity, elevated blood pressure, hyperlipidemia, impaired glucose tolerance, and other symptoms, the primary risk factor of which is insulin resistance. Such conditions are highly likely to lead to development of arteriosclerotic diseases and proteinuria, and may result in the development of nephropathy with glomerulus and renal tubular hypertrophy as histological features. When such a case is combined with apparent diabetes, the feature of hyperglycemia is further developed, diabetic nephropathy is manifested, and the disease conditions may further become serious. Type II diabetes is basically preceded by or simultaneously develops with metabolic syndrome. Accordingly, the feature of nephropathy could be included as nephropathy associated with metabolic syndrome.

Saito A. et al. have conducted an experiment using rat yolk sac epithelium-derived cells (L2 cells) in which megalin is expressed at high levels and found that incorporation of $^{125}$I-labelled AGE (advanced glycation end products) (derived from glucose) into L2 cells would be significantly inhibited by an anti-megalin antibody. Thus, they demonstrated that megalin is associated with a pathway for such incorporation (see Saito A. Gejyo F. et al., 2003, J. Am. Soc. Nephrol. 14, 1123-1131). As a mechanism of diabetic nephropathy development, association of advanced glycation end products (AGE) with glycated and modified proteins by the Maillard reaction has been pointed out. A low-molecular-weight AGE in the blood is filtered by glomeruli, and it is reabsorbed and metabolized by the proximal tubule epithelial cells. If nephropathy further advances, a higher-molecular weight AGE also is filtered by glomeruli, accumulates in the proximal tubule epithelial cells, and imposes excessive metabolic loads. Further, Saito A. et al. also demonstrate that megalin is also associated with incorporation of AGE derived from methylglyoxal, glyceraldehyde, or glycolaldehyde into cells, in addition to glucose. Also, metabolic syndrome is often complicated with hepatopathy, such as fatty liver. Liver type fatty acid binding proteins (L-FABP) that are abundantly present in the liver are released into the blood of a healthy person. In case of hepatopathy, more L-FABP is released into and increased in the blood. Saito A. et al. have also demonstrated that L-FABP in the blood is rapidly filtered by glomeruli and it is reabsorbed by the proximal tubule epithelial cells via megalin (see Takeda T., Gejyo F., Saito A. et al., 2005, Lab. Invest. 85, 522-531).

7. Functional Protein that Interacts with Megalin

In order to elucidate the mechanism of megalin transportation in cells, adaptor molecules that bind to megalin intracellular domains are searched for, and various proteins, such as Dab2, ANKRA, MAGI-1, GAIP, GIPC, Galphai3, MegBP, and ARH, have been identified (see Oleinikov A. V. et al., 2000, Biochem. J. 347, 613-621; Rader K., Farquhar M. G. et al., 2000, J. Am. Soc. Nephrol. 11, 2167-2178; Patrie K. M., Margolis B. et al., 2001, J. Am. Soc. Nephrol. 12, 667-677; Lou X., Farquhar M. G. et al., 2002, J. Am, Soc. Nephrol. 13, 918-927; Petersen H. H., Willnow T. E., 2003, J. Cell. Sci. 116, 453-461; and Takeda T., Farquhar M. G. et al., 2003, Mol. Biol. Cell. 14, 4984-4996). Through such molecules, megalin is associated with endocytosis or transcytosis, and megalin is also associated with signal transmission related thereto. Also, megalin functions conjugatively with a cell membrane receptor, i.e., cubilin, in the proximal tubule epithelial cells, so as to be further involved with incorporation of various ligands into cells (see Saito A. et al., 1994, Proc. Natl. Acad. Sci. U.S.A., 91, 9725-9729). For example, cubilin is a receptor that directly binds to transferrin, albumin, endogenous vitamin $B_{12}$, or the like, and megalin is indirectly involved with endocytosis thereof. Also, megalin is known to interact with the Na$^+$—H$^+$ exchanger isoform 3 (NHE3) in the proximal tubule epithelial cells (see Biemesderfer D. et al., 1999, J. Biol. Chem. 274, 17518-17524). NHE3 is an antiporter that plays an important role in reabsorption of Na+, and NHE3 also influences incorporation of a ligand by megalin (see Hryciw D. H. et al., 2004, Clin. Exp. Pharmacol. Physiol. 31, 372-379). Also, megalin may be involved with inactivation and metabolism of NHE3. At an early stage of diabetic nephropathy or metabolic syndrome-related nephropathy, glomerular filtration becomes excessive. Enhanced reabsorption of Na+ of the proximal tubule is deduced to be a primary cause (see Vallon V. et al., 2003, J. Am. Soc. Nephrol. 14, 530-537), NHE3 plays a key role in such a case, and inactivation and metabolism of MHE3 by megalin is considered to be involved therewith (see Hryciw D. H. et al., 2004, Clin. Exp. Pharmacol. Physiol. 31, 372-379).

8. Correlation of Urinary Excretion of Megalin and Urinary Excretion of Ligand by Megalin Leheste et al. disclosed that megalin-knockout mice and Fanconi syndrome patients with weakened proximal tubule functions would experience increased excretion of proteins and retinol in the urine (see Leheste J. et al., 1999, Am. J. Pathol. 155, 1361-1370). Further, Moestrup S. K. et al. demonstrated that the amount of megalin excreted in urine of patients of Fanconi syndrome is significantly lower than that excreted by healthy individuals. This causes deterioration of megalin functions and expression in the proximal tubule and consequently increases the amount of glomerular-filtered proteins containing retinol-binding proteins excreted in urine (see Anthony G. W., Moestrup S. K. et al., 2002, J. Am. Soc. Nephrol. 13, 125-133).

9. Importance of Megalin Function Found by Experiments Using Models For Uremia and Models for Organ Regeneration As described above, megalin is involved with intake of various low-molecular-weight proteins into the proximal tubule epithelial cells and metabolism thereof. When the pathological condition advances to kidney failure, the mechanism of the metabolism is disturbed, and low-molecular-weight proteins are consequently accumulated in the blood and tissues as uremic proteins. A representative example thereof is $\beta_2$-microglobulin ($\beta_2$-m), which may cause dialysis-related amyloidosis in a long-term dialysis patient (see Gejyo F., Schmid K. et al., 1985, Biochem. Biophys. Res. Commun. 129, 701-706). The aforementioned AGE is also suggested as a cause of arteriosclerosis or organ failure due to its accumulation in the blood of patients with kidney failure or dialysis, and AGE is considered as a type of uremic protein (see Henle T., Miyata T., 2003, Adv. Ren. Replace Ther. 10, 321-331). Further, leptin accumulates in the blood of a dialysis patient and thus is considered to be involved with malnutrition or immunity compromise. Tabata Y. and Gejyo F. et al. disclosed the effects and effectiveness of models for metabolizing uremic protein using megalin functions (see Saito A., Tabata Y., Gejyo F. et al., 2003, J. Am. Soc. Nephrol. 14, 2025-2032 and WO 02/091955). That is, megalin-expressing cells are transplanted as scaffold proteins in vivo, and low-molecular-weight proteins leaked from peripheral blood vessels (newborn blood vessels) are incorporated into the cells with the aid of megalin for metabolization. The megalin-expressing cells used for transplantation (i.e., yolk sac epithelium-derived L2 cells) incorporate and metabolize $\beta_2$-m with the aid of megalin (see Saito A., Tabata Y., Gejyo F. et al., 2003, J. Am. Soc. Nephrol. 14, 2025-2032). Both kidneys of a nude mouse into which L2 cells had been subcutaneously transplanted were removed, the condition of kidney failure was induced, and cell incorporation in the tissue mass into which $^{125}$I-labeled $\beta_2$-m had been transplanted and in organs via intraperitoneal injection was measured. As a result, the cell mass into which L2 cells had been transplanted was found to more significantly incorporate $^{125}$I-labeled $\beta_2$-m compared with other organs, and the $^{125}$I-labeled $\beta_2$-m clearance was found to significantly advance in a group to which L2 cells had been transplanted, compared with a control group into which L2 cells had not been transplanted (see Saito A., Tabata Y., Gejyo F. et al., 2003, J. Am. Soc. Nephrol. 14, 2025-2032).

10. Proteolysis and Urinary Excretion of Megalin

In recent years, the possibility of megalin being subjected to proteolysis in a Notch-like signaling pathway has been suggested (see Zou Z., Biemesderfer D. et al., 2004, J. Biol. Chem. 279, 34302-34310; and Grigorenko A. P. et al., 2004. Proc. Natl. Acad. Sci. U.S.A., 101, 14955-14960). This also includes a two-step cleavage system of shedding of an ectodomain mediated by metalloprotease and intramembrane proteolysis mediated by gamma-secretase.

Also, megalin is known to express in the type II alveolar cell.

Thus, megalin has been extensively studied in respect of its correlation with the metabolism in organs such as the kidney. However, the correlation between diseases of organs, including the kidney, and megalin has not yet been elucidated, and expression of megalin or excretion thereof to the body fluid in connection with a variety of organ diseases has not yet been studied.

To date, a method involving tissue staining or Western blotting using a polyclonal antibody obtained by immunizing an immune animal, such as a rabbit, has been known as a method for detecting megalin.

This technique, however, involves staining of a cell or a protein separated via electrophoresis, and this necessitates very complicated procedures and a long period of time for immobilizing tissues, preparing tissue slices, electrophoresis, and transfer onto the membrane. Thus, it is difficult to quantify megalin.

From the viewpoint of diagnosis of the degrees of functional disorders of tissues or organs, particularly in the case of kidney disorders, there is no effective means for diagnosing kidney tubule failure in a specific and simple manner. At present, many methods of diagnosis that detect albumin, creatinine. $\beta_2$-microglobulin, L-FABP, or the like in urine or blood as a diagnosis marker for renal diseases have been employed. Such diagnosis markers, however, are not derived from kidney tissue, and they merely result from all phenomenon and functions during filtration in kidney glomeruli and reabsorption in kidney tubules. That is, it is difficult to identify glomerulus failure and failure of kidney tubule failure in the kidney even with the use of such marker. Also, such marker is an indirect marker derived from organs other than the kidney. Thus, effectiveness is poor for early diagnosis of a disease. The same applies to KL-6 (markers of acute inflammation), which is an existing diagnosis marker for lung diseases, and particularly for inflammation.

DISCLOSURE OF THE INVENTION

The present invention provides a method for measuring human megalin that can be performed in a simpler manner within a shorter period of time than is possible with conventional techniques, and that can also quantify human megalin. Further, this method enables diagnosis of functional diseases, which are specific to cells, tissues, or organs, in a site-directed manner at an early stage. In particular, the present invention provides a method of measuring megalin levels in urine to detect kidney disorders.

As described above, many reports have been made regarding human megalin, and the correlation thereof with the metabolism of organs such as the kidney or the lung, has been suggested. When organ functions are impaired, however, the way that megalin expression varies and the way that prevalence of megalin changes are unknown.

The present inventors have conducted concentrated studies regarding a method for measuring human megalin with high sensitivity in a rapid manner. Consequently, they discovered a method for accurately measuring megalin in a body fluid sample, such as urine, using a ligand capable of binding to human megalin, and in particular, an anti-human megalin antibody.

Further, the present inventors measured human megalin in the body fluid of a patient with impaired organ functions and discovered that human megalin could be a marker for detecting and diagnosing organ diseases. This has led to the completion of the present invention.

Specifically, the present invention is as follows.

[1] A method for measuring human megalin in a sample using a first ligand capable of binding to human megalin that is bound to a solid support and a second ligand capable of binding to human megalin, the method comprising allowing the sample to react with the first ligand capable of binding to human megalin that is bound to a solid support, allowing the sample to react with the second ligand capable of binding to human megalin, and measuring the second ligand capable of binding to human megalin that is bound to a solid support resulting from formation of a complex of human megalin in the sample and the ligand capable of binding to human megalin.

[2] The method for measuring human megalin in a sample according to [1], which comprises the two steps of the reaction between the first ligand capable of binding to human megalin that is bound to a solid support and the sample and the following reaction between the second ligand capable of binding to human megalin and the sample.

[3] The method for measuring human megalin in a sample according to [1], wherein the reaction between the first ligand capable of binding to human megalin that is bound to a solid support and the sample and the reaction between the second ligand capable of binding to human megalin and the sample are carried out in a single step.

[4] The method for measuring human megalin in a sample according to any of [1] to [3], wherein the first ligand capable of binding to human megalin and the second ligand capable of binding to human megalin are both antibodies.

[5] The method for measuring human megalin in a sample according to any of [1] to [3], wherein the first ligand capable of binding to human megalin is lectin, which is specific to a sugar chain of human megalin, and the second ligand capable of binding to human megalin is an antibody.

[6] The method for measuring human megalin in a sample according to any of [1] to [3], wherein the first ligand capable of binding to human megalin is an antibody and the second ligand capable of binding to human megalin is lectin, which is specific to a sugar chain of human megalin.

[7] The method for measuring human megalin in a sample according to any of [1] to [6], wherein the first ligand capable of binding to human megalin and/or the second ligand capable of binding to human megalin are substances selected from the group consisting of: vitamin-binding protein, which is transcobalamin-vitamin $B_{12}$, vitamin-D-binding protein, or retinol-binding protein; lipoprotein, which is apolipoprotein B, apolipoprotein E, apolipoprotein J/clusterin, or apolipoprotein H; hormone, which is parathyroid hormone (PTH), insulin, epithelial growth factor (EGF), prolactin, leptin, or thyroglobulin, a receptor of any thereof, or a receptor of such hormone; immune or stress response-associated protein, which is immunoglobulin light chain, PAP-1, or $\beta_2$-microglobulin; enzyme, which is PAI-I, PAI-I-urokinase, PAI-I-tPA, prourokinase, lipoprotein lipase, plasminogen, $\alpha$-amylase, $\beta$-amylase, $\alpha_1$-microglobulin, or lysozyme, an inhibitor of any thereof, or an inhibitor of such enzyme; drug or toxin, which is aminoglycoside, polymyxin B, aprotinin, or trichosantin; carrier protein, which is albumin, lactoferrin, hemoglobin, odorant-binding protein, transthyretin, or L-FABP; and receptor-associated protein (RAP), which is cytochrome-c, calcium ($Ca^{2+}$), advanced glycation end products (AGE), cubilin, or $Na^+$—$H^+$ exchanger isoform 3 (NHE3) or binding fragment of such substance.

[8] A method for measuring human megalin in a sample using human megalin or a partial fragment of human megalin that is bound to a solid support and a ligand capable of binding to human megalin, the method comprising allowing the sample to react with the ligand capable of binding to human megalin, allowing the reaction product to react with the human megalin that is bound to a solid support, measuring the ligand capable of binding to human megalin that is bound to a solid support, and competitively quantifying human megalin in the sample based on a decrease in a percentage of the ligand capable of binding to human megalin that is bound to a solid support.

[9] The method for measuring human megalin in a sample according to [8], wherein the ligand capable of binding to human megalin is an anti-human megalin antibody.

[10] A method for measuring human megalin in a sample using a ligand capable of binding to human megalin, the method comprising allowing the sample to react with the ligand capable of binding to human megalin that is bound to a particle to induce agglutination and measuring human megalin based on the degree of resulting agglutination.

[11] The method for measuring human megalin according to [10], wherein the ligand capable of binding to human megalin is an anti-human megalin antibody and the agglutination is immune agglutination.

[12] A method of measuring human megalin by the method according to any of [1] to [11] to detect a disease in an organ in which megalin expression is observed.

[13] The method for detecting a disease in an organ according to [12], wherein the disease in an organ in which megalin expression is observed is a lung disease.

[14] The method for detecting a disease in an organ according to [12], wherein the disease in an organ in which megalin expression is observed is a renal disease.

[15] The method for detecting a renal disease according to [14], wherein the renal disease is renal tubular disorder.

[16] The method according to [14] or [15], wherein the sample is urine.

[17] A kit for detecting a disease in an organ in which megalin expression is observed comprising a ligand capable of binding to human megalin.

[18] The kit for detecting a disease in an organ in which megalin expression is observed according to [17], wherein the ligand capable of binding to human megalin is an anti-human megalin antibody.

[19] The kit for detecting a disease in an organ in which megalin expression is observed according to [18], wherein the disease in an organ in which megalin expression is observed is a lung disease.

[20] The kit for detecting a disease in an organ in which megalin expression is observed according to [18], wherein the disease in an organ in which megalin expression is observed is a renal disease.

[21] The kit for detecting a renal disease according to [20], wherein the renal disease is a renal tubular disorder.

[22] A disease-detecting marker for detecting a disease in an organ in which megalin expression is observed comprising human megalin.

[23] The disease-detecting marker according to [22], wherein the disease in an organ in which megalin expression is observed is a lung disease.

[24] The disease-detecting marker according to [22], wherein the disease in an organ in which megalin expression is observed is a renal disease.

[25] The disease-detecting marker according to [24], wherein the renal disease is a renal tubular disorder.

[26] Use of human megalin as a disease-detecting marker for detecting a disease in an organ in which megalin expression is observed.

[27] The use of human megalin as a disease-detecting marker according to [26], wherein the disease in an organ in which megalin expression is observed is a lung disease.

[28] The use of human megalin as a disease-detecting marker according to [26], wherein the disease in an organ in which megalin expression is observed is a renal disease.

[29] The use of human megalin as a disease-detecting marker according to [28], wherein the renal disease is a renal tubular disorder.

Effects of the Invention

The method of the present invention enables measurement of human megalin in a sample, such as urine, with high sensitivity and accuracy. When functions of megalin-expressing cells, tissues, or organs are damaged, megalin escapes from the cells and accumulates in a sample. Specifically, measurement of human megalin in a sample enables direct detection and diagnosis of functional disorders of cells, tissues, or organs instead of indirect detection and diagnosis. Accordingly, measurement of human megalin in a sample via the method of the present invention enables detection of a disease in an organ in which megalin expression is observed, such as a renal or lung disease, at an early stage with high accuracy.

This description includes part or all of the contents as disclosed in the description and/or drawings of Japanese Patent Application No. 2006-089306, which is a priority document of the present application.

BEST MODES FOR CARRYING OUT THE INVENTION

Figure 1:
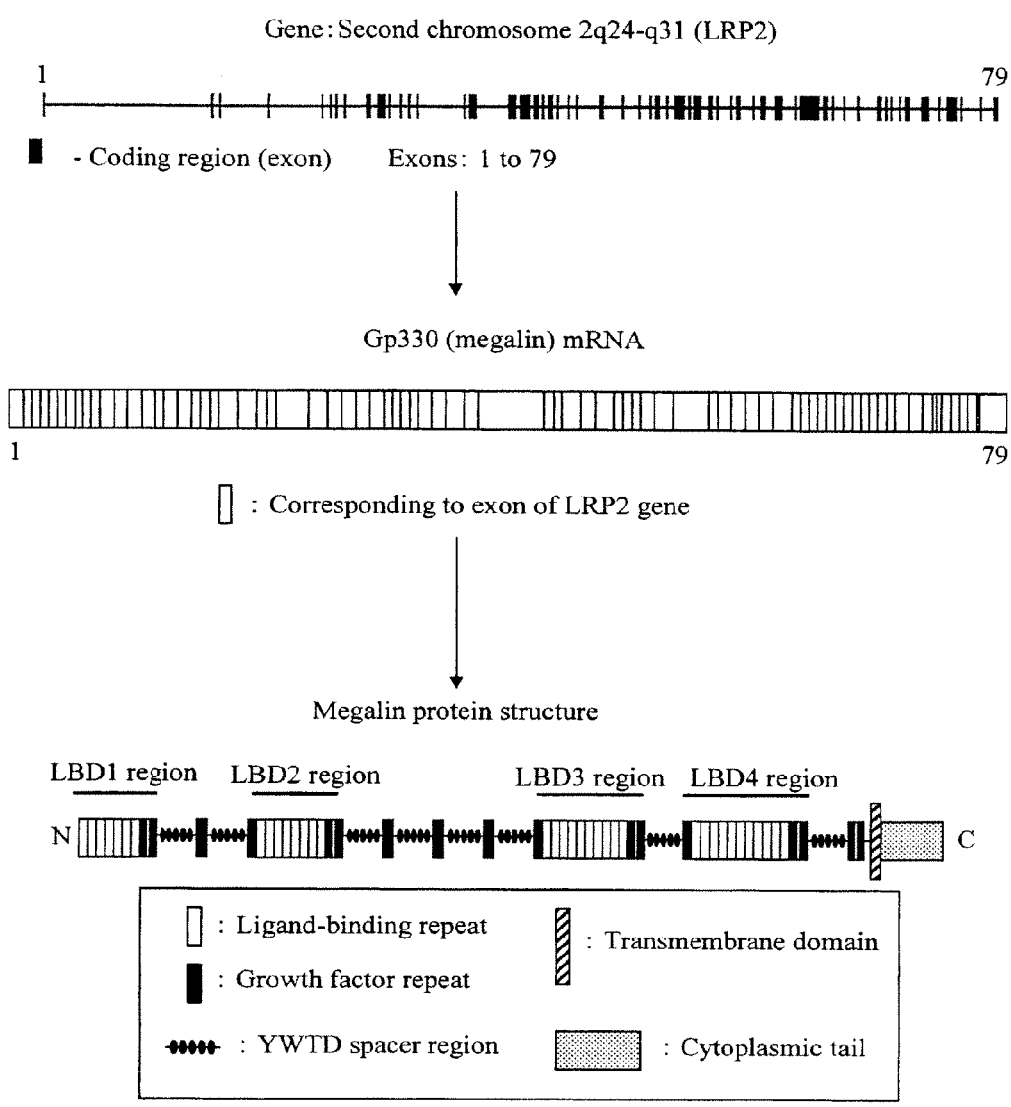
FIG. 1 shows a gene locus and a general protein structure of human megalin.

The present invention concerns a method for measuring human megalin in a sample. SEQ ID NO: 1 shows the nucleotide sequence of human megalin, and SEQ ID NO: 2 shows the amino acid sequence of human megalin.

In the present invention, human megalin is measured using a first ligand capable of binding to human megalin that is bound to a solid support. Any solid support used in conventional immunoanalysis can be used. For example, wells of a plastic microtiter plate or magnetic particles can be preferably used.

An example of a ligand capable of binding to human megalin is an anti-human megalin antibody, and a monoclonal or polyclonal antibody can be used.

Also, lectin that is specific to a sugar chain of human megalin can be used as a ligand capable of binding to human megalin. Examples of lectin include, but are not limited to, concanavalin A, wheat germ lectin (WGA), *Ricinus communis* lectin (RCA), and lentil lectin (LCA).

Further, examples of a ligand capable of binding to human megalin include substances selected from the group consisting of: vitamin-binding proteins, such as transcobalamin-vitamin $B_{12}$, vitamin-D-binding protein, or retinol-binding protein; lipoproteins, such as apolipoprotein B, apolipoprotein E, apolipoprotein J/clusterin, or apolipoprotein H; hormones, such as parathyroid hormone (PTH), insulin, epithelial growth factor (EGF), prolactin, leptin, or thyroglobulin, a receptor of any thereof, or a receptor of such hormone; immune or stress response-associated proteins, such as immunoglobulin light chain, PAP-1, or $\beta_2$-microglobulin; enzymes, such as PAI-I, PAI-I-urokinase, PAI-I-tPA, prourokinase, lipoprotein lipase, plasminogen, $\alpha$-amylase, $\beta$-amylase, $\alpha_1$-microglobulin, or lysozyme, an inhibitor of any thereof, or an inhibitor of such enzyme; drugs or toxins, such as aminoglycoside, polymyxin B, aprotinin, or trichosantin; carrier proteins, such as albumin, lactoferrin, hemoglobin, odorant-binding protein, transthyretin, or L-FABP; and receptor-associated proteins (RAP), such as cytochrome-c, calcium ($Ca^{2+}$), advanced glycation end products (AGE), cubilin, or $Na^+$—$H^+$ exchanger isoform 3 (NHE3) or binding fragments of such substances. The term "binding fragment" used herein refers to a fragment of the aforementioned substance that includes a site binding to human megalin.

A ligand capable of binding to human megalin, such as an anti-human megalin antibody, can be bound to a solid support by a technique well-known in the art. When a ligand is to be bound to microtiter plate wells, for example, about 3 to 10 μg/ml (preferably about 5 μg/ml) of a solution of a ligand capable of binding to human megalin, such as an antibody, is applied to a solid support and the resultant is then allowed to stand at 4° C. overnight (preferably 12 hours or longer). The recommended density of a solid support mentioned above was theoretically determined when immobilizing a full-length antibody.

The density is determined by theoretical formulae:

$$Q = (2/\sqrt{3}) \cdot (MW/N) \cdot (2r)^{-2} \cdot 10^9 \text{ (ng/cm}^2\text{)}$$

Q: molecular weight density (ng/cm$^2$)
MW: molecular weight (dalton: Da)
N: Avogadro's number=$6 \cdot 10^{23}$ (mole$^{-1}$)
r: Stokes radius of molecular=$(R \cdot T_{20})/(6 \cdot \pi \cdot \eta_{20} \cdot D_{20} \cdot N)$ (cm)
R: gas constant=$8.3 \cdot 10^7$ (g·cm$^2$·sec$^{-2}$·°K$^{-1}$·mole$^{-1}$)
$T_{20}$: room temperature (20° C.)=293° K.
$\eta_{20}$: viscosity of water at 20° C.=$1 \cdot 10^{-2}$ (g·cm$^{-1}$·sec$^{-1}$)
$D_{20}$: diff. coeff. of molecular ref. to water at 20° C. (cm$^2$·sec$^{-1}$)

Such value is applied when immobilizing via physical adsorption. When a ligand capable of binding to human megalin is immobilized, the theoretical density of the relevant solid support is determined, and such density is affected by the aforementioned variation factors, such as individual molecular weight. Thus, the density varies depending on type of individual solid-support molecule, configuration of solid phase, or other conditions. Accordingly, the density is not limited to the aforementioned values. When absorbed on a solid support via covalent binding, also, such density is utilized in the present invention. In such a case, the number of functional groups that are present on the adsorption surface and used for covalent binding is also taken into consideration. The density of a solid support is not limited. After binding, blocking is carried out using bovine serum albumin (hereafter abbreviated to "BSA") or casein, for the purpose of blocking non-specific adsorption sites of a protein, based on a conventional technique. When a solid support is a magnetic bead, the solid support is treated in the same manner as in the case of a microtiter plate.

A ligand capable of binding to human megalin, such as an anti-human megalin antibody, bound to a solid support is allowed to react with a sample, and human megalin in a sample is bound to a solid support with the aid of the ligand capable of binding to human megalin bound to the solid support by a ligand-receptor binding reaction, such as an antigen-antibody reaction. Specifically, a complex of a first ligand capable of binding to human megalin, such as an anti-human megalin antibody, bound to a solid support and human megalin is formed. Any sample may be used, provided that it contains human megalin. Examples of a sample include urine, an alveolar wash, blood, blood serum, blood plasma, and an exhaled air condensate. Such antigen-antibody reaction can be carried out at 4° C. to 45° C., more preferably 20° C. to 40° C., and further preferably 25° C. to 38° C. The duration of the reaction is approximately 10 minutes to 18 hours, more preferably 10 minutes to 1 hour, and further preferably 30 minutes to 1 hour.

After washing, the second ligand capable of binding to human megalin is then allowed to react with the human megalin in a sample bound to a solid support. Specifically, a complex of a first ligand capable of binding to human megalin, such as an anti-human megalin antibody, bound to a solid support, human megalin, and a second ligand capable of binding to human megalin is formed. As the second ligand capable of binding to human megalin, the same substance used as the first ligand capable of binding to human megalin, such as an anti-human megalin antibody, can be used. However, when both the first ligand capable of binding to human megalin and the second ligand capable of binding to human megalin are anti-human megalin monoclonal antibodies, an epitope that is recognized and bound by the first anti-human megalin antibody needs to be different from an epitope that is recognized and bound by the second anti-human megalin antibody. A combination of the first anti-human megalin antibody and the second anti-human megalin antibody can be any combination of a monoclonal antibody and a monoclonal antibody, a monoclonal antibody and a polyclonal antibody, a polyclonal antibody and a monoclonal antibody, and a polyclonal antibody and polyclonal antibody. The reaction can be carried out at 4° C. to 45° C., more preferably 20° C. to 40° C., and further preferably 25° C. to 38° C. The duration of the reaction is about 10 minutes to 18 hours, more preferably 10 minutes to 1 hour, and further preferably 30 minutes to 1 hour. Thus, the second ligand capable of binding to human megalin is bound to a solid support with the aid of human megalin and the first ligand capable of binding to human megalin.

After washing, the second ligand capable of binding to human megalin, such as the second anti-human megalin antibody, bound to a solid support is then measured. This can be carried out via a variety of techniques that are commonly employed in the immunoanalysis field. For example, the second ligand capable of binding to human megalin is labeled with an enzyme, fluorescence, biotin, or radiation label to prepare an enzyme-labeled substance. By assaying such label, the second ligand capable of binding to human megalin bound to a solid support can be measured. Labeling with an enzyme or fluorescence is particularly preferable. Examples of enzyme include peroxidase, alkaline phosphatase, β-galactosidase, and glucose oxidase, and an example of fluorescence is fluorescein isothiocyanate (FITC), although labels are not limited thereto. A label can be detected by allowing a relevant substrate to react with an enzyme-labeled substance and then measuring the resulting dye, fluorescence, emission, or the like. When the second ligand capable of binding to human megalin is not labeled, a labeled third antibody is allowed to react with the second ligand capable of binding to human megalin, and the third antibody can be measured based on such labeling. Thus, the second ligand capable of binding to human megalin can be measured.

A solid support or an anti-human megalin antibody used for labeling may be an immunoglobulin fragment, such as Fab or F(ab')$_2$, specific to human megalin or a recombinant antibody, such as scFv, dsFv, diabody, or minibody, expressed as a recombinant. In the present invention, the term "antibody" also refers to a fragment specific to human megalin. A method for preparing such fragment is well-known in the art.

The aforementioned method comprises the two steps of the reaction between a first ligand capable of binding to human megalin, such as an anti-human megalin antibody, bound to a solid support and a sample, followed by washing, and the reaction of a second ligand capable of binding to human megalin with a sample. Alternatively, a method comprising a single step in which the reaction between a first ligand capable of binding to human megalin, such as an anti-human megalin antibody, bound to a solid support and a sample is carried out simultaneously with the reaction between a second ligand capable of binding to human megalin and a sample.

The present invention further comprises a method for measuring human megalin in a sample using human megalin or a partial fragment of human megalin that is bound to a solid support and a ligand capable of binding to human megalin, the method comprising allowing a sample to react with a ligand capable of binding to human megalin, allowing the reaction product to react with the human megalin that is bound to a solid support, measuring the ligand capable of binding to human megalin that is bound to a solid support, and competitively quantifying human megalin in a sample based on a decrease in a percentage of the ligand capable of binding to human megalin that is bound to a solid support. This method requires binding of human megalin to a solid support, and such binding can be carried out in accordance with the method for binding a substance to a solid support. Also, a partial fragment of human megalin is not limited, and a partial fragment of human megalin to which a ligand capable of binding to human megalin is bound may be used. As a partial fragment of human megalin, a partial sequence of the amino acid sequence of human megalin as shown in SEQ ID NO: 2 can be prepared via chemical synthesis or genetic engineering. The aforementioned ligand capable of binding to human megalin can be used, and an anti-human megalin antibody is particularly preferable. In a competitive method, the amount of human megalin or a partial fragment of human megalin that is bound to a solid support and a ligand capable of binding to human megalin to be used is important. A competitive method is a known technique, and such amount can be adequately determined based on a known technique.

Further, the present invention comprises a method for measuring human megalin using a ligand capable of binding to human megalin, the method comprising allowing a sample to react with a ligand capable of binding to human megalin that is bound to a particle to induce agglutination and measuring human megalin based on the degree of resulting agglutination.

Examples of particles that are used in such method include particles having diameters of 0.05 to 10 μm, preferably latex particles having diameters of 0.1 to 0.4 μm, gelatin particles having diameters of 0.5 to 10 μm, and animal erythrocytes. An antibody can be bound to a particle by a method well-known in the art, such as physical adsorption or covalent binding.

In this method, particles comprising anti-human megalin antibodies bound thereto are mixed with a sample on, for example, a black glass slide, and particles precipitated as a result of agglutination are observed. Thus, human megalin in a sample can be detected. Also, the absorption of the agglutinate may be measured to quantify human megalin. Further, human megalin can also be detected via pulse immunoassay.

The method for measuring human megalin of the present invention enables measurement of not only intact human megalin but also fragments of human megalin.

By measuring human megalin in a sample, whether or not a subject from which a sample has been obtained has disorders in human megalin-expressing cells, tissues, organs, or the like can be evaluated. Specifically, an organ disease or the like can be detected or diagnosed.

Any cells, tissues, or organs may be targets, provided that megalin expression is observed therein. Lung and kidney are preferable, and kidney is further preferable. In case of renal diseases, nephritis or renal tubular disorder can be particularly detected. Also, diabetic nephropathy can be adequately detected. Further, such cells, tissues, or organs can also be used for detecting metabolic syndrome or metabolic syndrome-associated nephropathy.

In the aforementioned subject having functional disorders of cells, tissues, or organs, human megalin escapes from cells and the amount of human megalin in a sample is increased. When human megalin in a sample obtained from the subject is measured in vitro and the concentration of human megalin in a sample is significantly enhanced compared with the concentration of human megalin obtained from a healthy individual, the subject can be diagnosed as having a functional disorder of cells, tissues, or organs.

As described above, urine, an alveolar wash, blood, blood serum, blood plasma, an exhaled air condensate, and the like can be used as samples. When a lung disease is to be detected, use of an alveolar wash is particularly preferable. When a renal disease is to be detected, use of urine is preferable.

Further, measurement of human megalin in a sample obtained from a subject enables evaluation of the risk of being afflicted with functional disorders of cells, tissues, or organs, such as a renal disease. When human megalin in a sample obtained from the subject is measured in vitro and the concentration of human megalin in a sample is significantly enhanced compared with the concentration of human megalin obtained from a healthy individual, the subject can be evaluated as being highly likely to be afflicted with functional disorders of cells, tissues, or organs. That is, measurement of human megalin in a sample enables screening for of subjects who are highly likely to be afflicted with a disease, such as patients-to-be of renal disease, and provision of adequate treatment.

Further, periodical measurement of human megalin in a sample obtained from the subject and monitoring of human megalin concentration enable management of organ functions.

Human megalin can be used as a marker for detecting or diagnosing functional disorders in cells, tissues, or organs where human megalin expression is observed. The present invention comprises use of human megalin as a marker for detecting a functional disorder, i.e., a disease in an organ in which megalin expression is observed. The present invention further comprises a disease-detecting/diagnosing marker for detecting and diagnosing a functional disorder, i.e., a disease in a cell, tissue, or an organ in which megalin expression is observed.

Also, when detecting or diagnosing a functional disorder, i.e., a disease in a cell, tissue, or an organ in which megalin expression is observed, fragments of human megalin may be measured, as well as intact human megalin.

EXAMPLES

Hereafter, the present invention is described in greater detail with reference to the examples, although the present invention is not limited to these examples. It should be noted that the method of enzyme-linked immunosorbent assay (ELISA) used in the examples has been heretofore reported by many researchers, since Engvall E. and Perlmann P. made the first report in 1971. There are solid grounds for using this technique (Engvall E, Perlmann P., 1971, Immunochemistry, 8, 871-874).

Hereafter, the present invention is described in greater detail with reference to the examples, although the present invention is not limited to these examples. Detection of human megalin in urine via enzyme-linked immunosorbent assay (ELISA)

(1) Preparation of Mouse Anti-Human Megalin Monoclonal Antibody

A mouse was immunized intraperitoneally with 50 μg of human megalin with an adjuvant several times, and the elevated blood serum titer was confirmed. The spleen was removed 3 days after a booster shot (intravenous immunization), and spleen cells were obtained. The spleen cells were fused with mouse myeloma cells (10:1) in the presence of polyethylene glycol 3500 to prepare hybridoma cells. The resulting cells were cultured for a week in the presence of $CO_2$ at 37° C., and the presence or absence of an anti-human megalin antibody in the culture supernatant was inspected. The cells in the positive wells in which antibody production was observed were diluted via limiting dilution, the resultants were cultured for 2 weeks, and the presence or absence of an anti-human megalin antibody in the culture supernatant was inspected in the same manner. Thereafter, the cells in the positive wells in which antibody production was observed were diluted via limiting dilution, and the resultants were cultured in the same manner. At this stage, cells in which anti-human megalin antibodies have been produced are cultured in a flask, part thereof is suspended in fetal calf serum (FCS) containing 10% dimethyl sulfoxide (DMSO) ($5\times10^6$ cells/ml), and the resultant was stored in liquid nitrogen.

Subsequently, supernatants in the wells were used to inspect reactivity of antibodies against human megalin produced in culture supernatants. Human megalin was dissolved in 140 mM NaCl, 2.7 mM KCl, 10 mM $Na_2HPO_4$, and 1.8 mM $KH_2PO_4$ (pH 7.3; hereafter abbreviated as "PBS, pH 7.3"). To wells of a plastic microtiter plate (Nunc-Immuno™ Module F8 Maxisorp™ Surface plate, Nalge Nunc International), 100 μl of the solution of human megalin in PBS (pH 7.3) was added per well, and human megalin was then immobilized on the microtiter plate at 3 pmol/well at 4° C. for 12 hours. Thereafter, the solution of human megalin in PBS (pH 7.3) that had been added to the wells was removed via decantation, 145 mM NaCl, 3.6 mM $Na_2HPO_4$, 1.4 mM $KH_2PO_4$, and 0.05% (v./v.) Tween 20 (hereafter abbreviated as "PBS-T") were applied to wells of the microtiter plate at 200 μl/well, PBS-T was removed via decantation, and the excessively adsorbed human megalin in the wells was washed. This process of washing was carried out twice in total. Thereafter, 145 mM NaCl, 7.2 mM $Na_2HPO_4$, 2.8 mM $KH_2PO_4$, 1% (wt./v.) BSA, and 5% (wt./v.) lactose (hereafter abbreviated as a "blocking solution for an antigen-immobilized plate) were applied at 200 μl/well, and insides of the wells of the microtiter plate on which human megalin had been immobilized were blocked at 4° C. for 12 hours. Thereafter, the resultant was stored at 4° C. In order to inspect the reactivity of antibodies in the culture supernatant, the microtiter plate on which human megalin had been immobilized after blocking treatment was used. To wells of the microtiter plate on which human megalin had been immobilized, a hybridoma culture supernatant was added at 100 μl/well, and the plate was heated at 37° C. for 1 hour. Thereafter, the culture supernatant that had been applied to the wells was removed via decantation, PBS-T was applied to the wells of the microtiter plate at 200 μl/well, PBS-T was removed via decantation, and insides of the wells were then washed. This process of washing was carried out three times in total. Thereafter, peroxidase-conjugated goat anti-mouse immunoglobulins (DAKO) were applied to the wells at 100 μl/well (2,000-fold diluted, 0.55 μg/ml), and the resultant was heated at 37° C. for 1 hour. The enzyme-labeled antibody was diluted using 145 mM NaCl, 3.6 mM $Na_2HPO_4$, 1.4 mM $KH_2PO_4$, 0.05% (v./v.) Tween 20, and 0.5% (wt./v.) BSA (hereafter referred to as a "diluent of enzyme-labeled antibody"). Thereafter, the enzyme-labeled antibodies that had been applied to the wells were removed via decantation, PBS-T was applied to the wells of the microtiter plate at 200 μl/well, PBS-T was removed via decantation, and insides of the wells were then washed. This process of washing was carried out three times in total. Thereafter, a 3,3',5,5'-tetramethylbenzidine (hereafter abbreviated as "TMB") solution (TMB One-Step Substrate System: DAKO) was applied to the wells at 100 μl/well as a substrate solution for peroxidase enzyme reaction, and the resultant was allowed to stand at 25° C. for 30 minutes. Immediately thereafter, a 313 mM $H_2SO_4$ solution (hereafter referred to as a "reaction terminator") was applied at 100 μl/well to the substrate solution for reaction in the wells to terminate the enzyme reaction in the wells. Thereafter, the absorption of the wells was measured, and the value obtained by subtracting the absorption at 630 nm from that at 450 nm was designated as an indicator for evaluation of reactivity (Josephy P. D., Mason R. P. et al., 1982, J. Biol. Chem. 257, 3669-3675). Many reports have been heretofore made regarding TMB-based colorimetry since Bos E. S. et al made the first report in 1981, and there are solid grounds for using this technique (Bos E. S. et al., 1981, J. Immunoassay, 2, 187-204).

As a result, monoclonalized hybridoma cells exhibiting strong reactivity of an anti-human megalin antibody to immobilized human megalin were selected, and the class and the subclass of immunoglobulin in the culture supernatant were examined regarding each clone from 100 μl of the stock culture supernatant solution using the mouse immunoglobulin typing kit (Wako Pure Chemical Industries, Ltd.). Based on the results, clones of the IgG class were selected from the resulting monoclone cell library and then the process of ascites preparation was carried out as described below.

Subsequently, these cells were cultured in a 25-ml flask and then in a 75-ml flask. The cells were injected intraperitoneally into a pristane-treated mouse, and ascites was sampled.

(2) Purification of Mouse Anti-Human Megalin Monoclonal (IgG) Antibody

The obtained ascites (10 ml) was mixed with an opacified blood serum-treating agent (FRIGEN (registered trademark) II: Kyowa Pure Chemical Co., Ltd.) at a ratio of 1:1.5 by volume, and the resultant was shaken and stirred for 1 to 2 minutes to delipidize the ascites. The ascites was centrifuged using a centrifuger at 3,000 rpm (1930×g) for 10 minutes, and the centrifuged supernatant of clarified ascites (10 ml) was fractionated. The centrifuged supernatant of ascites (10 ml) was subjected to ammonium sulfate fractionation (final concentration: 50% saturated ammonium sulfate) in an ice bath for 1 hour, and the precipitated immunoglobulin fraction was suspended and dissolved in PBS. This process of ammonium sulfate fractionation was carried out twice in total to obtain a crude immunoglobulin fraction from ascites. The resulting crude immunoglobulin fraction (10 ml) was mixed with an equivalent amount of 20 mM sodium phosphate (pH 7.0; hereafter referred to as "20 mM NaPB (pH 7.0)" and then subjected to affinity purification using a protein G column (HiTrap Protein G HP, 5 ml; Amersham BioSciences)). The sample was adsorbed on a protein G column, 20 mM NaPB (pH 7.0, 50 ml) was flushed through the protein G column, and contaminants other than IgG in the sample were removed by washing. Thereafter, affinity-adsorbed IgG on the protein G column was eluted with 0.1 M glycine-HCl (pH 2.7), and the elution fraction immediately after elution from the column was neutralized with 1M tris(hydroxymethyl)aminomethane-HCl (pH 9.0) and then recovered (hereafter "tris (hydroxymethyl)aminomethane" is abbreviated as "Tris"). After neutralization, the affinity-purified product was dialyzed against PBS in an amount 500 times greater than the purified product by volume at 4° C. for 6 hours, and this process of dialysis was carried out twice in total. The dialysis membrane used for dialysis was a cellulose tube for dialysis (Viskase Companies). The resulting IgG elution fraction was designated as a purified anti-human megalin monoclonal antibody and subjected to storage at 4° C. and procedures described below. The process of purification was performed by connecting the aforementioned protein G column to the BioLogic LP System (Bio Rad Laboratories) at a constant flow rate of 1 ml/min.

(3) Preparation of Microtiter Plate on which Anti-Human Megalin Monoclonal Antibody has been Immobilized The purified anti-human megalin monoclonal antibody was dissolved in PBS (pH 7.3) to result in a final concentration of 5 μg/ml therein. To wells of a plastic microtiter plate (Nunc-Immuno™ Module F8 Maxisorp™ Surface plate, Nalge Nunc International), 100 μl of the solution of the anti-human megalin monoclonal antibody in PBS (pH 7.3) was added per well, and the anti-human megalin monoclonal antibody was immobilized on the microtiter plate at 4° C. for 12 hours. Thereafter, the solution of the anti-human megalin monoclonal antibody in PBS (pH 7.3) that had been added to the wells was removed via decantation, PBS-T was added to the wells of the microtiter plate at 200 μl/well, PBS-T was removed via decantation, and the excessively adsorbed anti-human megalin monoclonal antibody in the wells was washed. This process of washing was carried out twice in total. Thereafter, 86 mM NaCl, 100 mM Tris, 0.5% (wt./v.) BSA, and 0.05% (v./v.) Tween 20 (hereafter referred to as a blocking solution for an antibody-immobilized plate) were added at 200 μl/well, and the insides of the wells of the human megalin-immobilized microtiter plate were subjected to blocking at 4° C. for 12 hours. Thereafter, the resultant was stored at 4° C.

(4) Preparation of Peroxidase-Labeled Anti-Human Megalin Monoclonal Antibody

Horseradish peroxidase (hereafter abbreviated as "HRP") (peroxidase from horseradish, Type VI, Sigma) was dissolved in pure water at a concentration of 4 mg/ml, 100 μl of a 100 mM sodium metaperiodate solution was added to 500 μl of the HRP solution (2 mg), and the mixture was agitated at room temperature for 20 minutes. The resultant was dialyzed against a 1 mM sodium acetate (pH 4.0) solution (hereafter referred to as a "1 mM acetate buffer") in an amount 500 times greater than that of the HRP solution by volume at 4° C. for 6 hours, and this procedure was performed twice. The dialysis membrane used for dialysis was a cellulose tube for dialysis (Viskase Companies). Subsequently, the anti-human megalin monoclonal antibody was dissolved in a solution of 2.4 mM $Na_2CO_3$ and 7.6 mM $NaHCO_3$ (pH 9.6) (hereafter referred to as a "10 mM carbonate buffer") at a concentration of 8 mg/ml. A solution of 120 mM $Na_2CO_3$ and 380 mM $NaHCO_3$ (pH 9.6) (hereafter referred to as a "0.5 M carbonate buffer") was added to 500 μl of the HRP solution (2 mg) in an amount one-third thereof by volume, 500 μl of the aforementioned anti-human megalin monoclonal antibody (4 mg) was added thereto, and the resultant was agitated at room temperature for 2 hours. Thereafter, 50 μl of a solution of sodium borohydride (4 mg/ml) was added, and the resultant was agitated in an ice bath for 2 hours. The resultant was subjected to ammonium sulfate fractionation (final concentration: 50% saturated ammonium sulfate) in an ice bath for 1 hour, and the precipitated fraction was suspended and dissolved in 1 ml of a solution of 100 mM Tris, 145 mM NaCl, and 1% (v./v.) BSA (pH 7.6) (hereafter referred to as a "suspension of labeled antibody"). This ammonium sulfate fractionation was carried out twice in total, and a solution of 2.8 mM $KH_2PO_4$, 7.2 mM Na$_2$HPO$_4$, 145 mM NaCl, 1% (wt./v.) BSA, 0.02% (v./v.) phenol, and 40% (wt./v.) D-sorbitol (hereafter referred to as a labeled-antibody stock solution) was added to the solution of the labeled antibody in an amount three-fourths of the solution of the labeled antibody (hereafter referred to as a labeled-antibody stock solution). The HRP-labeled anti-human megalin monoclonal antibody was obtained. Many reports have been heretofore made regarding the method of HRP labeling, ever since Nakane, P. K. and Kawaoi, A. made the first report in 1974. Thus, there are solid grounds for using this technique (Nakane, P. K., Kawaoi, A., 1974, J. Histochem. Cytochem. 22, 1084).

(5) Measurement of Human Megalin in Urine

Figure 2:
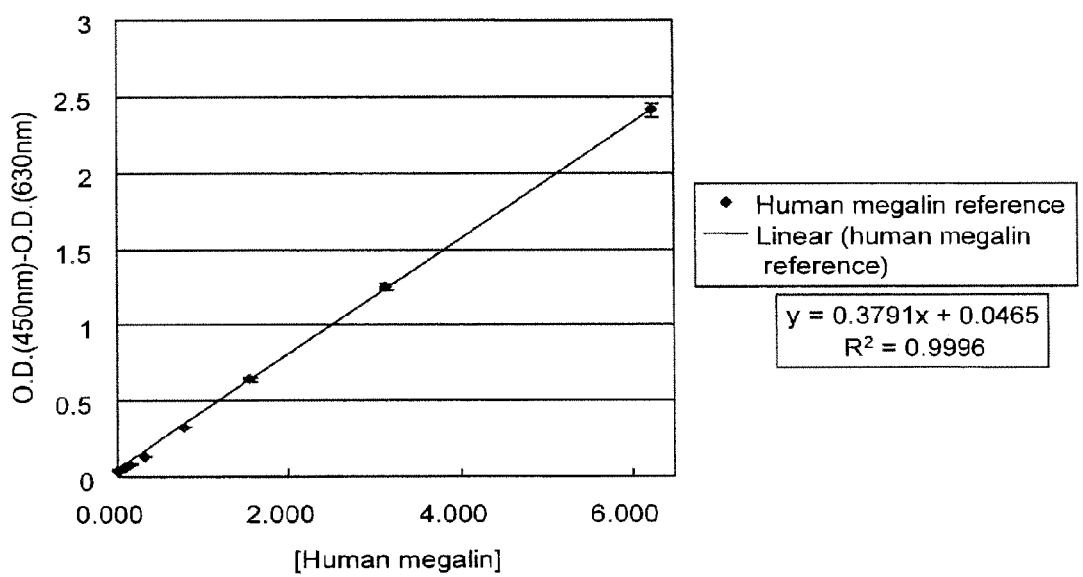
FIG. 2 shows an ELISA calibration curve for detecting human megalin with the use of standard human megalin.
Figure 3:
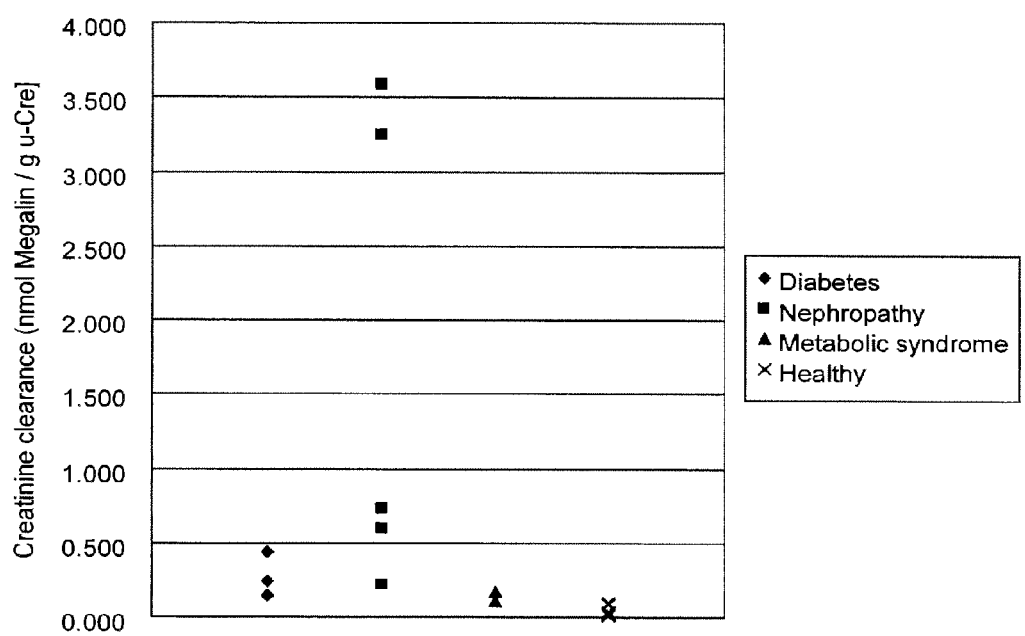
FIG. 3 shows the clinical results of human megalin in urine (part 1).
Figure 4:
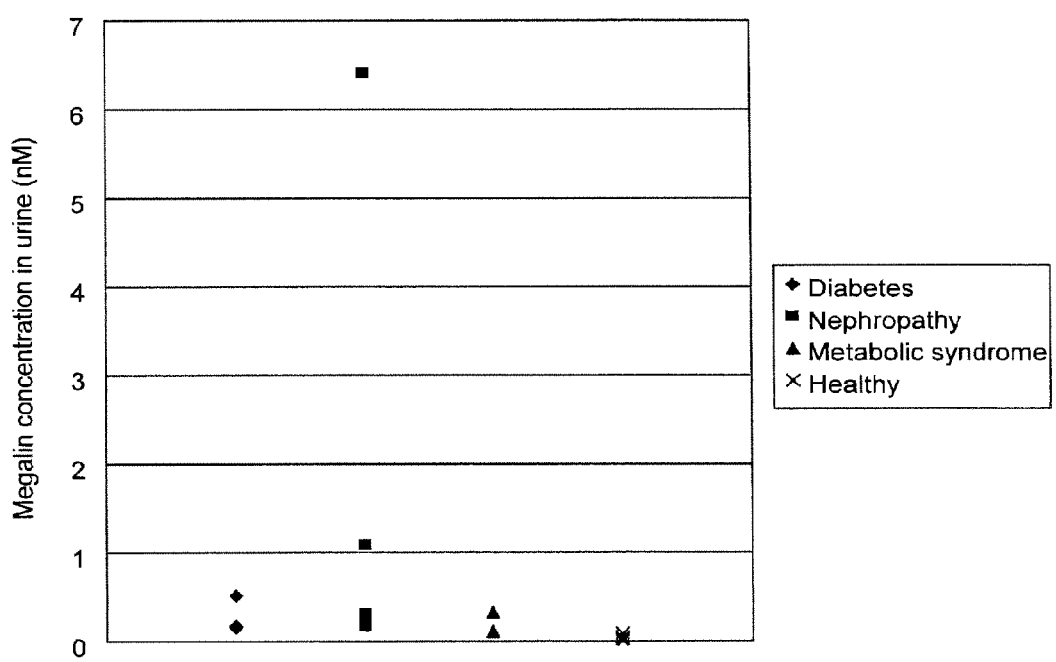
FIG. 4 shows the clinical results of human megalin in urine (part 2).

The aforementioned anti-human megalin monoclonal antibody-immobilized microtiter plate and the HRP-labeled anti-human megalin monoclonal antibody were used to measure human megalin in urine. At the outset, 90 μl of glomerular filtrate was mixed with 10 μl of a solution of 2 M Tris and 0.2 Methylenediamine-N,N,N',N'-tetraacetic acid (hereafter "ethylenediamine-N,N,N',N'-tetraacetic acid" is abbreviated as EDTA, pH 8.0), and 100 μl of the resulting solution was applied to wells of the microtiter plate to which the anti-human megalin monoclonal antibody has been immobilized. The resultant was allowed to stand at 37° C. for 1 hour, the urine sample solution that had been applied to wells was removed via decantation, PBS-T was applied to wells of the microtiter plate at 200 μl/well, and PBS-T was removed via decantation. followed by washing. The process of washing was carried out three times. Thereafter, the solution of HRP-labeled anti-human megalin monoclonal antibody (the above stock solution was diluted to 10,000-fold with the solution of diluted labeled antibody) was added at 100 μl/well. The resultant was allowed to stand at 37° C. for 1 hour, the solution of HRP-labeled antibody that had been applied to the wells was removed via decantation, PBS-T was added to wells of the microtiter plate at 200 μl/well, and PBS-T was removed via decantation, followed by washing. The process of washing was carried out three times. Subsequently, a TMB solution (TMB One-Step Substrate System; DAKO) was applied to wells as a substrate solution for peroxidase enzyme reaction at 100 μl/well, and the resultant was allowed to stand at 25° C. for 30 minutes. Immediately thereafter, the reaction terminator was added to the substrate solution in the wells at 100 μl/well to terminate the enzyme reaction in the wells. Thereafter, the absorbance of the wells was measured, and the value obtained by subtracting the absorbance at 630 nm from that at 450 nm was designated as an indicator for evaluation of measurement of human megalin in the urine. As the reference sample for the calibration curve, human megalin that was used as an immunological antigen at the time of preparation of an anti-human megalin monoclonal antibody was used, and the results of analysis are shown in Table 1 and FIG. 2. The results of actual clinical measurement of human megalin in the urine are shown in Table 2, FIG. 3, and FIG. 4. As a result, the amount of human megalin excreted to the urine was found to be significantly greater in patients with renal diseases and patient-to-be of renal diseases, compared with healthy individuals (FIGS. 3 and 4). The results of the creatinine clearance tests regarding the amount of megalin excreted to the urine were also similar. This indicates that the concentration at the time of urinary excretion would not matter (FIGS. 3 and 4). The present invention provides a method for measuring human megalin that can be performed in a simpler manner within a shorter period of time than is possible with conventional techniques, and that can also quantify human megalin. Further, this method enables diagnosis of functional diseases that are specific to cells, tissues, or organs, in a site-directed manner at an early stage. The clinical results shown above apparently support such feature of the present invention.

TABLE 1

| [h-megalin] | ELISA calibration curve for detecting human megalin | | | | |
|---|---|---|---|---|---|
| (nM) | n = 1 | n = 2 | n = 3 | AVR. | S.D. |
| 6.250 | 2.4356 | 2.4416 | 2.3576 | 2.4116 | 0.0469 |
| 3.125 | 1.2551 | 1.2596 | 1.2261 | 1.2469 | 0.0182 |
| 1.563 | 0.6288 | 0.6576 | 0.6358 | 0.6407 | 0.0150 |
| 0.781 | 0.3282 | 0.3296 | 0.3282 | 0.3287 | 0.0008 |
| 0.313 | 0.1341 | 0.1359 | 0.1370 | 0.1357 | 0.0015 |
| 0.156 | 0.0788 | 0.0917 | 0.0858 | 0.0854 | 0.0065 |
| 0.078 | 0.0582 | 0.0638 | 0.0727 | 0.0649 | 0.0073 |
| 0.031 | 0.0390 | 0.0503 | 0.0468 | 0.0454 | 0.0058 |
| 0.000 | 0.0465 | 0.0409 | 0.0431 | 0.0435 | 0.0028 |

TABLE 2

| Item Method of measurement | | Creatinine in urine Enzyme method: Color method | Megalin in urine ELISA | | |
|---|---|---|---|---|---|
| Background of samples | Sample No. | [u-Cre] (mg/dl) | O.D. (450 nm)-O.D. (630 nm) | [Megalin] (nM) | Creatinine clearance (nmol megalin/g Cre) |
| Diabetes | D-1 | 117.96 | 0.241 | 0.513 | 0.435 |
| | D-2 | 68.16 | 0.110 | 0.168 | 0.246 |
| | D-3 | 102.53 | 0.102 | 0.146 | 0.142 |
| Nephropathy | N-1 | 178.52 | 2.472 | 6.398 | 3.584 |
| | N-2 | 33.55 | 0.459 | 1.088 | 3.243 |
| | N-3 | 41.24 | 0.161 | 0.302 | 0.732 |
| | N-4 | 78.29 | 0.110 | 0.168 | 0.215 |
| | N-5 | 36.97 | 0.129 | 0.218 | 0.590 |
| Metabolic syndrome | M-1 | 302.32 | 0.169 | 0.323 | 0.107 |
| | M-2 | 59.56 | 0.086 | 0.104 | 0.175 |
| Healthy individuals | H-1 | 44.11 | 0.061 | 0.038 | 0.086 |
| | H-2 | 92.72 | 0.082 | 0.094 | 0.101 |
| | H-3 | 134.72 | 0.056 | 0.025 | 0.019 |
| | H-4 | 123.59 | 0.063 | 0.044 | 0.036 |
| | H-5 | 104.31 | 0.052 | 0.015 | 0.014 |
| | H-6 | 96.64 | 0.050 | 0.009 | 0.009 |

All publications, patents, and patent applications cited herein are incorporated herein by reference in their entirety.

The invention claimed is:

1. A method for early stage detecting and treating a renal disease, which method comprises:
   (i) determining a human megalin level in a urine sample;
   (ii) screening for a patient who suffers from or is at high risk of the renal disease indicated by an increased level of human megalin in a urine sample in comparison to the human megalin level in a healthy subject; and
   (iii) treating the patient identified by step (ii),
   wherein the renal disease is selected from the group consisting of nephritis, nephropathy, and a renal tubular disorder.

2. The method of claim 1, wherein the human megalin level is determined by a ligand binding assay.

3. The method of claim 2, wherein the ligand is capable of binding to human megalin and is selected from the group consisting of an anti-human megalin antibody, a lectin that is specific to a sugar chain of human megalin, a vitamin-binding protein, a lipoprotein, a hormone, insulin, epithelial growth factor (EGF), prolactin, leptin, thyroglobulin, an immune or stress response-associated protein, an enzyme, a toxin, a carrier protein, and a receptor-associated protein.

4. The method of claim 1, wherein step (iii) comprising administering to the patient a steroid, an antibiotic, an immunosuppressive drug, or a combination thereof.

* * * * *